United States Patent
Britt et al.

(10) Patent No.: US 10,004,183 B2
(45) Date of Patent: Jun. 26, 2018

(54) SYSTEM AND METHOD FOR AN INTERNET OF THINGS (IOT) MOISTURE SENSOR

(71) Applicant: Afero, Inc., Los Altos, CA (US)

(72) Inventors: Joe Britt, Los Altos, CA (US); Omar Zakaria, Santa Clara, CA (US); Alec Storrie-Lombardi, Sunnyvale, CA (US)

(73) Assignee: Afero, Inc., Los Altos, CA (US)

( * ) Notice: Subject to any disclaimer, the term of this patent is extended or adjusted under 35 U.S.C. 154(b) by 322 days.

(21) Appl. No.: 14/727,804

(22) Filed: Jun. 1, 2015

(65) Prior Publication Data

US 2016/0345516 A1    Dec. 1, 2016

(51) Int. Cl.
| | |
|---|---|
| *A01G 25/16* | (2006.01) |
| *G01N 33/24* | (2006.01) |
| *G05B 15/02* | (2006.01) |
| *G01N 27/04* | (2006.01) |

(52) U.S. Cl.
CPC .......... *A01G 25/167* (2013.01); *G01N 33/24* (2013.01); *G05B 15/02* (2013.01); *G01N 27/048* (2013.01)

(58) Field of Classification Search
CPC .... A01G 25/167; G01N 27/048; G01N 33/24; G05B 15/02
See application file for complete search history.

(56) References Cited

U.S. PATENT DOCUMENTS

| | | | | |
|---|---|---|---|---|
| 5,813,606 A | * | 9/1998 | Ziff | A01G 25/167 239/63 |
| 8,862,277 B1 | * | 10/2014 | Campbell | A01G 25/167 324/664 |
| 2004/0106202 A1 | * | 6/2004 | Zainiev | A61F 13/02 436/39 |
| 2010/0109685 A1 | * | 5/2010 | Morton | G01N 33/246 324/696 |

(Continued)

FOREIGN PATENT DOCUMENTS

| | | | |
|---|---|---|---|
| CN | 205485512 U | * | 8/2016 |
| KR | 100977438 B1 | * | 8/2010 |

OTHER PUBLICATIONS

International Search Report and Written Opinion for Application No. PCT/US2016/035159 dated Aug. 31, 2016, 11 pages.

(Continued)

*Primary Examiner* — Francis Gray
(74) *Attorney, Agent, or Firm* — Nicholson De Vos Webster & Elliott LLP

(57) ABSTRACT

An apparatus and method are described for a moisture sensor. For example, one embodiment of an IoT device comprises: An Internet of Things (IoT) device comprising: a moisture sensor to detect a moisture level; an IoT communication interface and/or radio to wirelessly connect the IoT device to a network; a set of pins, pads, and/or probes to electrically couple the moisture sensor to conductive elements of one or more moisture sensor attachments; and an enclosure surrounding the moisture sensor and IoT com- (Continued)

munication interface and/or radio, the enclosure having one or more connection elements formed thereon to fixedly couple one or more moisture sensor attachments to the enclosure, thereby electrically coupling the set of pins, pads, and/or probes of the moisture sensor to the conductive elements of the moisture sensor attachments.

19 Claims, 20 Drawing Sheets

(56) References Cited

U.S. PATENT DOCUMENTS

| | | | |
|---|---|---|---|
| 2010/0241279 A1* | 9/2010 | Samon i Castella | A01G 25/16 700/284 |
| 2014/0018002 A1* | 1/2014 | Jose | H04W 4/008 455/41.2 |
| 2015/0081058 A1* | 3/2015 | Oliver | A63F 13/245 700/91 |
| 2015/0351337 A1* | 12/2015 | Sabadin | A01G 25/16 700/282 |

OTHER PUBLICATIONS

Wireless Sensor Network for Precision Irrigation Gontrol in Horticultural Crops, ASABE, 2012 Dallas, Texas, Jul. 29 Aug. 1, 2012 121337892.(doi:10.1303112013.41846). (retrieved on Aug. 1, 2016) Retrieved from the interent: URL: https://www.researchgate.net/profile/Linda_Dodge/publication/266503082_ Wireless_Sensor_Network_for_Precision_Irrigation_ Control_in_Horticultural_Crops/links/ 54f8e5c70cf2ccffe9df5ffe.pdf.

International Preliminary Report on Patentability for Application No. PCT/US2016/035159, dated Dec. 14, 2017, 10 pages.

* cited by examiner

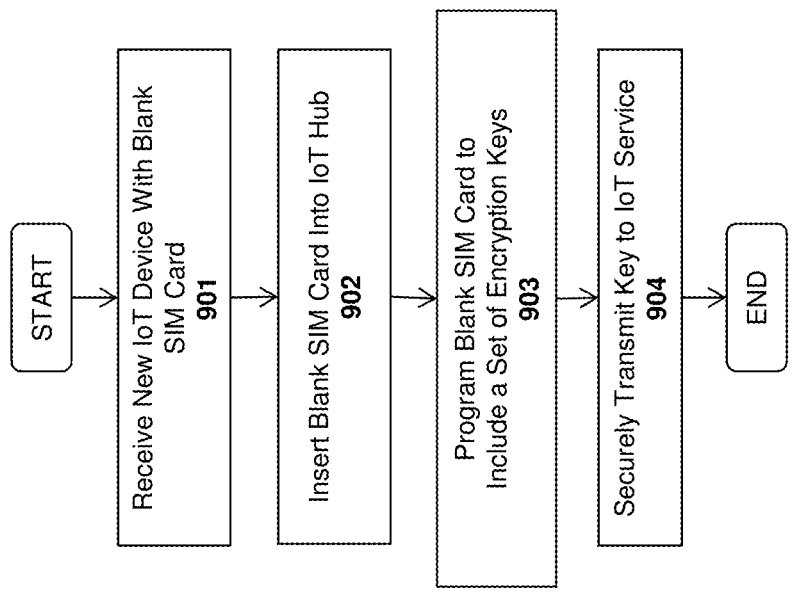

(12) United States Patent
US 10,004,183 B2

SYSTEM AND METHOD FOR AN INTERNET OF THINGS (IOT) MOISTURE SENSOR

BACKGROUND

Field of the Invention

This invention relates generally to the field of computer systems. More particularly, the invention relates to a system and method for an Internet of Things (IoT) moisture sensor.

Description of the Related Art

The "Internet of Things" refers to the interconnection of uniquely-identifiable embedded devices within the Internet infrastructure. Ultimately, IoT is expected to result in new, wide-ranging types of applications in which virtually any type of physical thing may provide information about itself or its surroundings and/or may be controlled remotely via client devices over the Internet.

Moisture sensors are currently available which measure the moisture content of the surrounding environment. In one common form, the sensor is formed with a long metal spike which is forced into the ground to measure moisture of the surrounding soil. A moisture level indicator coupled to at the top of the spike provides an indication of the moisture level.

BRIEF DESCRIPTION OF THE DRAWINGS

A better understanding of the present invention can be obtained from the following detailed description in conjunction with the following drawings, in which:

FIG. 9 illustrates one embodiment of a method for programming a SIM using an IoT hub;

DETAILED DESCRIPTION

In the following description, for the purposes of explanation, numerous specific details are set forth in order to provide a thorough understanding of the embodiments of the invention described below. It will be apparent, however, to one skilled in the art that the embodiments of the invention may be practiced without some of these specific details. In other instances, well-known structures and devices are shown in block diagram form to avoid obscuring the underlying principles of the embodiments of the invention.

One embodiment of the invention comprises an Internet of Things (IoT) platform which may be utilized by developers to design and build new IoT devices and applications. In particular, one embodiment includes a base hardware/software platform for IoT devices including a predefined networking protocol stack and an IoT hub through which the IoT devices are coupled to the Internet. In addition, one embodiment includes an IoT service through which the IoT hubs and connected IoT devices may be accessed and managed as described below. In addition, one embodiment of the IoT platform includes an IoT app or Web application (e.g., executed on a client device) to access and configured the IoT service, hub and connected devices. Existing online retailers and other Website operators may leverage the IoT platform described herein to readily provide unique IoT functionality to existing user bases.

Figure 1A:
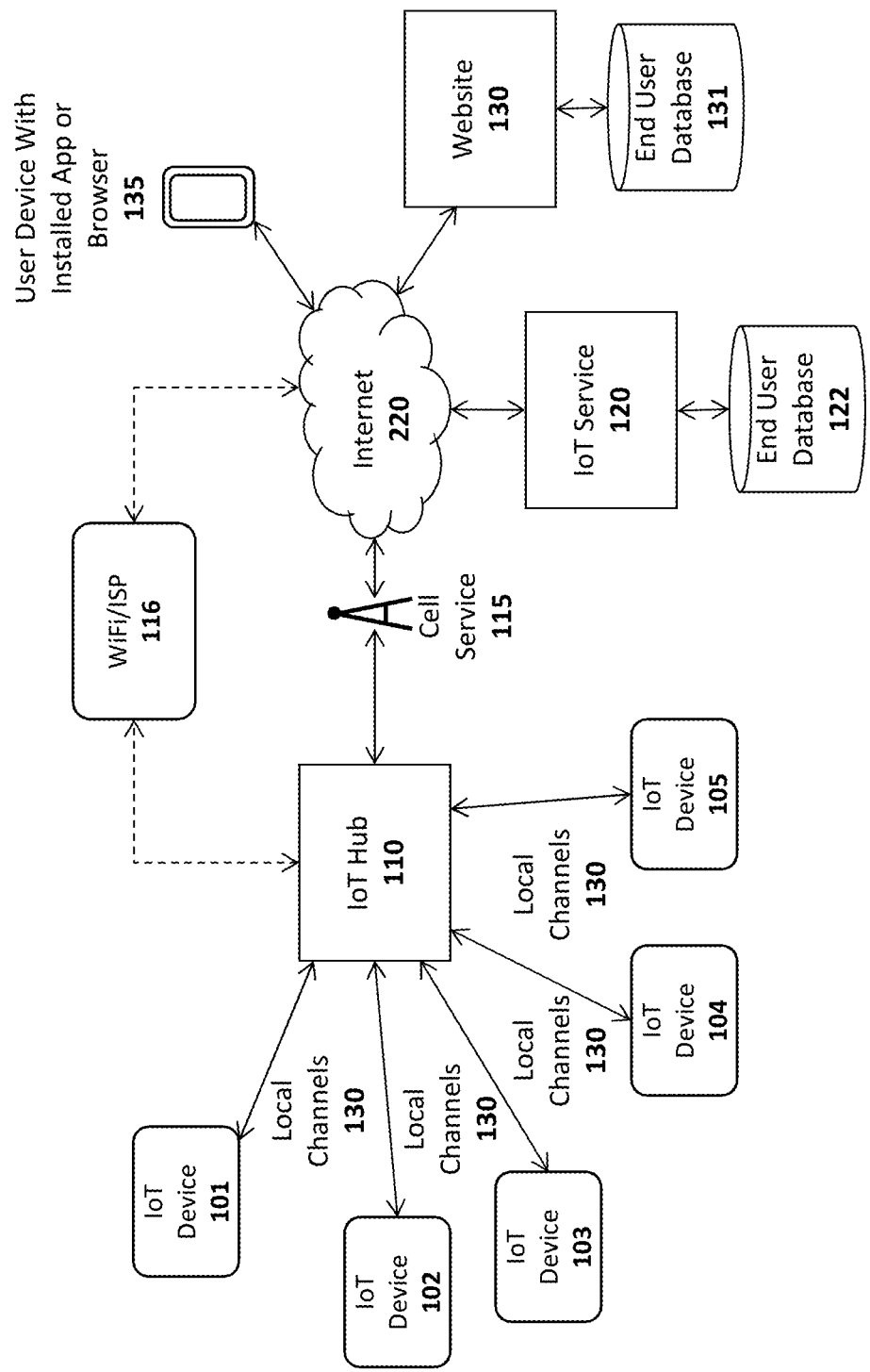
FIGS. 1A-B illustrates different embodiments of an IoT system architecture.

FIG. 1A illustrates an overview of an architectural platform on which embodiments of the invention may be implemented. In particular, the illustrated embodiment includes a plurality of IoT devices 101-105 communicatively coupled over local communication channels 130 to a central IoT hub 110 which is itself communicatively coupled to an IoT service 120 over the Internet 220. Each of the IoT devices 101-105 may initially be paired to the IoT hub 110 (e.g., using the pairing techniques described below) in order to enable each of the local communication channels 130. In one embodiment, the IoT service 120 includes an end user database 122 for maintaining user account information and data collected from each user's IoT devices. For example, if the IoT devices include sensors (e.g., temperature sensors, accelerometers, heat sensors, motion detectore, etc), the database 122 may be continually updated to store the data collected by the IoT devices 101-105. The data stored in the database 122 may then be made accessible to the end user via the IoT app or browser installed on the user's device 135 (or via a desktop or other client computer system) and to web clients (e.g., such as websites 130 subscribing to the IoT service 120).

The IoT devices 101-105 may be equipped with various types of sensors to collect information about themselves and their surroundings and provide the collected information to the IoT service 120, user devices 135 and/or external Websites 130 via the IoT hub 110. Some of the IoT devices 101-105 may perform a specified function in response to control commands sent through the IoT hub 110. Various specific examples of information collected by the IoT devices 101-105 and control commands are provided below. In one embodiment described below, the IoT device 101 is a user input device designed to record user selections and send the user selections to the IoT service 120 and/or Website.

In one embodiment, the IoT hub 110 includes a cellular radio to establish a connection to the Internet 220 via a cellular service 115 such as a 4G (e.g., Mobile WiMAX, LTE) or 5G cellular data service. Alternatively, or in addition, the IoT hub 110 may include a WiFi radio to establish a WiFi connection through a WiFi access point or router 116 which couples the IoT hub 110 to the Internet (e.g., via an Internet Service Provider providing Internet service to the end user). Of course, it should be noted that the underlying principles of the invention are not limited to any particular type of communication channel or protocol.

In one embodiment, the IoT devices 101-105 are ultra low-power devices capable of operating for extended periods of time on battery power (e.g., years). To conserve power, the local communication channels 130 may be implemented using a low-power wireless communication technology such as Bluetooth Low Energy (LE). In this embodiment, each of the IoT devices 101-105 and the IoT hub 110 are equipped with Bluetooth LE radios and protocol stacks.

As mentioned, in one embodiment, the IoT platform includes an IoT app or Web application executed on user devices 135 to allow users to access and configure the connected IoT devices 101-105, IoT hub 110, and/or IoT service 120. In one embodiment, the app or web application may be designed by the operator of a Website 130 to provide IoT functionality to its user base. As illustrated, the Website may maintain a user database 131 containing account records related to each user.

Figure 1B:
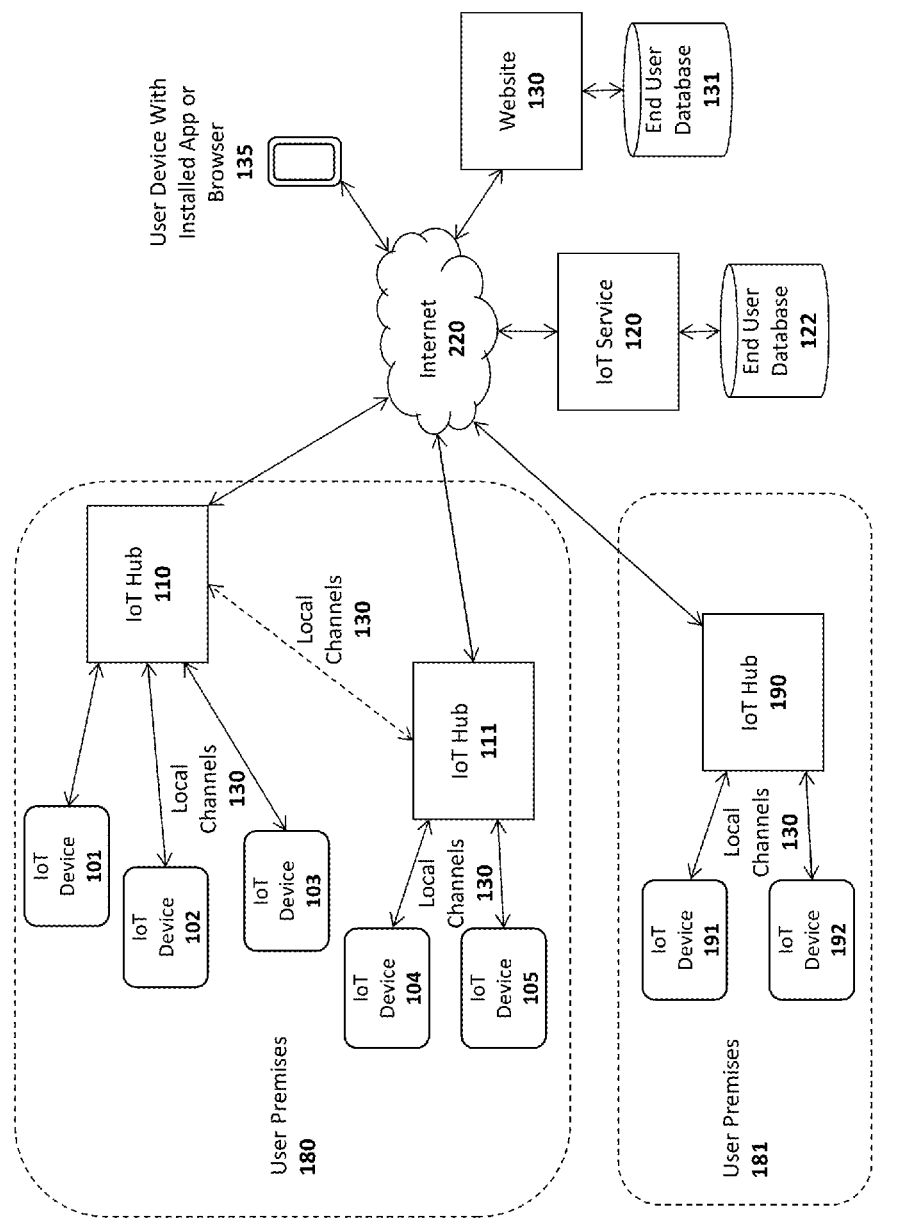

FIG. 1B illustrates additional connection options for a plurality of IoT hubs 110-111, 190 In this embodiment a single user may have multiple hubs 110-111 installed onsite at a single user premises 180 (e.g., the user's home or business). This may be done, for example, to extend the wireless range needed to connect all of the IoT devices 101-105. As indicated, if a user has multiple hubs 110, 111 they may be connected via a local communication channel (e.g., Wifi, Ethernet, Power Line Networking, etc). In one embodiment, each of the hubs 110-111 may establish a direct connection to the IoT service 120 through a cellular 115 or WiFi 116 connection (not explicitly shown in FIG. 1B). Alternatively, or in addition, one of the IoT hubs such as IoT hub 110 may act as a "master" hub which provides connectivity and/or local services to all of the other IoT hubs on the user premises 180, such as IoT hub 111 (as indicated by the dotted line connecting IoT hub 110 and IoT hub 111). For example, the master IoT hub 110 may be the only IoT hub to establish a direct connection to the IoT service 120. In one embodiment, only the "master" IoT hub 110 is equipped with a cellular communication interface to establish the connection to the IoT service 120. As such, all communication between the IoT service 120 and the other IoT hubs 111 will flow through the master IoT hub 110. In this role, the master IoT hub 110 may be provided with additional program code to perform filtering operations on the data exchanged between the other IoT hubs 111 and IoT service 120 (e.g., servicing some data requests locally when possible).

Regardless of how the IoT hubs 110-111 are connected, in one embodiment, the IoT service 120 will logically associate the hubs with the user and combine all of the attached IoT devices 101-105 under a single comprehensive user interface, accessible via a user device with the installed app 135 (and/or a browser-based interface).

In this embodiment, the master IoT hub 110 and one or more slave IoT hubs 111 may connect over a local network which may be a WiFi network 116, an Ethernet network, and/or a using power-line communications (PLC) networking (e.g., where all or portions of the network are run through the user's power lines). In addition, to the IoT hubs 110-111, each of the IoT devices 101-105 may be interconnected with the IoT hubs 110-111 using any type of local network channel such as WiFi, Ethernet, PLC, or Bluetooth LE, to name a few.

FIG. 1B also shows an IoT hub 190 installed at a second user premises 181. A virtually unlimited number of such IoT hubs 190 may be installed and configured to collect data from IoT devices 191-192 at user premises around the world. In one embodiment, the two user premises 180-181 may be configured for the same user. For example, one user premises 180 may be the user's primary home and the other user premises 181 may be the user's vacation home. In such a case, the IoT service 120 will logically associate the IoT hubs 110-111, 190 with the user and combine all of the attached IoT devices 101-105, 191-192 under a single comprehensive user interface, accessible via a user device with the installed app 135 (and/or a browser-based interface).

Figure 2:
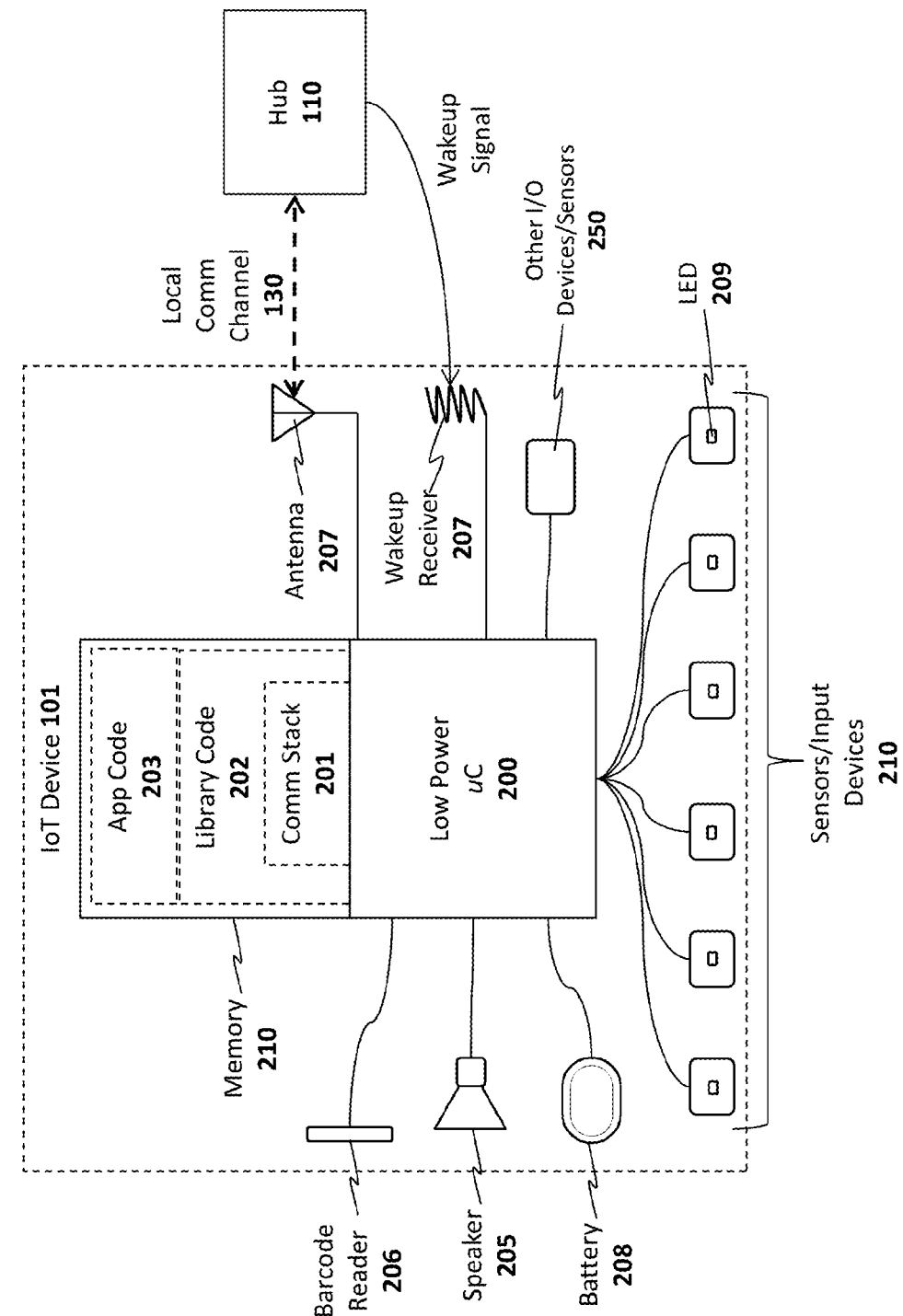
FIG. 2 illustrates an IoT device in accordance with one embodiment of the invention.

As illustrated in FIG. 2, an exemplary embodiment of an IoT device 101 includes a memory 210 for storing program code and data 201-203 and a low power microcontroller 200 for executing the program code and processing the data. The memory 210 may be a volatile memory such as dynamic random access memory (DRAM) or may be a non-volatile memory such as Flash memory. In one embodiment, a non-volatile memory may be used for persistent storage and a volatile memory may be used for execution of the program code and data at runtime. Moreover, the memory 210 may be integrated within the low power microcontroller 200 or may be coupled to the low power microcontroller 200 via a bus or communication fabric. The underlying principles of the invention are not limited to any particular implementation of the memory 210.

As illustrated, the program code may include application program code 203 defining an application-specific set of functions to be performed by the IoT device 201 and library code 202 comprising a set of predefined building blocks which may be utilized by the application developer of the IoT device 101. In one embodiment, the library code 202 comprises a set of basic functions required to implement an IoT device such as a communication protocol stack 201 for enabling communication between each IoT device 101 and the IoT hub 110. As mentioned, in one embodiment, the communication protocol stack 201 comprises a Bluetooth LE protocol stack. In this embodiment, Bluetooth LE radio and antenna 207 may be integrated within the low power microcontroller 200. However, the underlying principles of the invention are not limited to any particular communication protocol.

The particular embodiment shown in FIG. 2 also includes a plurality of input devices or sensors 210 to receive user input and provide the user input to the low power microcontroller, which processes the user input in accordance with the application code 203 and library code 202. In one embodiment, each of the input devices include an LED 209 to provide feedback to the end user.

In addition, the illustrated embodiment includes a battery 208 for supplying power to the low power microcontroller. In one embodiment, a non-chargeable coin cell battery is used. However, in an alternate embodiment, an integrated rechargeable battery may be used (e.g., rechargeable by connecting the IoT device to an AC power supply (not shown)).

A speaker 205 is also provided for generating audio. In one embodiment, the low power microcontroller 299 includes audio decoding logic for decoding a compressed audio stream (e.g., such as an MPEG-4/Advanced Audio Coding (AAC) stream) to generate audio on the speaker 205.

Alternatively, the low power microcontroller 200 and/or the application code/data 203 may include digitally sampled snippets of audio to provide verbal feedback to the end user as the user enters selections via the input devices 210.

In one embodiment, one or more other/alternate I/O devices or sensors 250 may be included on the IoT device 101 based on the particular application for which the IoT device 101 is designed. For example, an environmental sensor may be included to measure temperature, pressure, humidity, etc. A security sensor and/or door lock opener may be included if the IoT device is used as a security device. Of course, these examples are provided merely for the purposes of illustration. The underlying principles of the invention are not limited to any particular type of IoT device. In fact, given the highly programmable nature of the low power microcontroller 200 equipped with the library code 202, an application developer may readily develop new application code 203 and new I/O devices 250 to interface with the low power microcontroller for virtually any type of IoT application.

In one embodiment, the low power microcontroller 200 also includes a secure key store for storing encryption keys for encrypting communications and/or generating signatures. Alternatively, the keys may be secured in a subscriber identify module (SIM).

Figure 3:
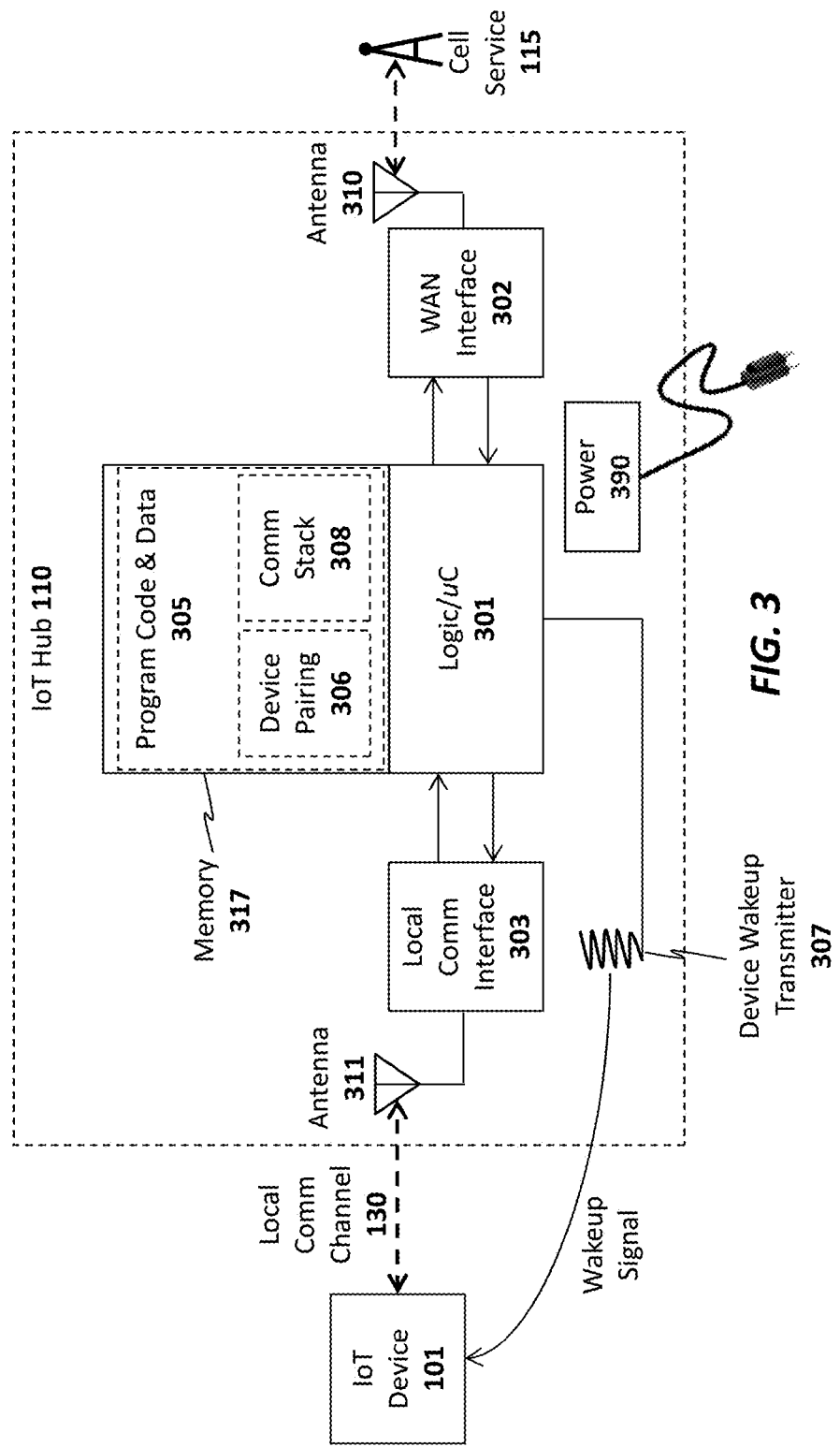
FIG. 3 illustrates an IoT hub in accordance with one embodiment of the invention.

A wakeup receiver 207 is included in one embodiment to wake the IoT device from an ultra low power state in which it is consuming virtually no power. In one embodiment, the wakeup receiver 207 is configured to cause the IoT device 101 to exit this low power state in response to a wakeup signal received from a wakeup transmitter 307 configured on the IoT hub 110 as shown in FIG. 3. In particular, in one embodiment, the transmitter 307 and receiver 207 together form an electrical resonant transformer circuit such as a Tesla coil. In operation, energy is transmitted via radio frequency signals from the transmitter 307 to the receiver 207 when the hub 110 needs to wake the IoT device 101 from a very low power state. Because of the energy transfer, the IoT device 101 may be configured to consume virtually no power when it is in its low power state because it does not need to continually "listen" for a signal from the hub (as is the case with network protocols which allow devices to be awakened via a network signal). Rather, the microcontroller 200 of the IoT device 101 may be configured to wake up after being effectively powered down by using the energy electrically transmitted from the transmitter 307 to the receiver 207.

As illustrated in FIG. 3, the IoT hub 110 also includes a memory 317 for storing program code and data 305 and hardware logic 301 such as a microcontroller for executing the program code and processing the data. A wide area network (WAN) interface 302 and antenna 310 couple the IoT hub 110 to the cellular service 115. Alternatively, as mentioned above, the IoT hub 110 may also include a local network interface (not shown) such as a WiFi interface (and WiFi antenna) or Ethernet interface for establishing a local area network communication channel. In one embodiment, the hardware logic 301 also includes a secure key store for storing encryption keys for encrypting communications and generating/verifying signatures. Alternatively, the keys may be secured in a subscriber identify module (SIM).

A local communication interface 303 and antenna 311 establishes local communication channels with each of the IoT devices 101-105. As mentioned above, in one embodiment, the local communication interface 303/antenna 311 implements the Bluetooth LE standard. However, the underlying principles of the invention are not limited to any particular protocols for establishing the local communication channels with the IoT devices 101-105. Although illustrated as separate units in FIG. 3, the WAN interface 302 and/or local communication interface 303 may be embedded within the same chip as the hardware logic 301.

In one embodiment, the program code and data includes a communication protocol stack 308 which may include separate stacks for communicating over the local communication interface 303 and the WAN interface 302. In addition, device pairing program code and data 306 may be stored in the memory to allow the IoT hub to pair with new IoT devices. In one embodiment, each new IoT device 101-105 is assigned a unique code which is communicated to the IoT hub 110 during the pairing process. For example, the unique code may be embedded in a barcode on the IoT device and may be read by the barcode reader 106 or may be communicated over the local communication channel 130. In an alternate embodiment, the unique ID code is embedded magnetically on the IoT device and the IoT hub has a magnetic sensor such as an radio frequency ID (RFID) or near field communication (NFC) sensor to detect the code when the IoT device 101 is moved within a few inches of the IoT hub 110.

In one embodiment, once the unique ID has been communicated, the IoT hub 110 may verify the unique ID by querying a local database (not shown), performing a hash to verify that the code is acceptable, and/or communicating with the IoT service 120, user device 135 and/or Website 130 to validate the ID code. Once validated, in one embodiment, the IoT hub 110 pairs the IoT device 101 and stores the pairing data in memory 317 (which, as mentioned, may include non-volatile memory). Once pairing is complete, the IoT hub 110 may connect with the IoT device 101 to perform the various IoT functions described herein.

In one embodiment, the organization running the IoT service 120 may provide the IoT hub 110 and a basic hardware/software platform to allow developers to easily design new IoT services. In particular, in addition to the IoT hub 110, developers may be provided with a software development kit (SDK) to update the program code and data 305 executed within the hub 110. In addition, for IoT devices 101, the SDK may include an extensive set of library code 202 designed for the base IoT hardware (e.g., the low power microcontroller 200 and other components shown in FIG. 2) to facilitate the design of various different types of applications 101. In one embodiment, the SDK includes a graphical design interface in which the developer needs only to specify input and outputs for the IoT device. All of the networking code, including the communication stack 201 that allows the IoT device 101 to connect to the hub 110 and the service 120, is already in place for the developer. In addition, in one embodiment, the SDK also includes a library code base to facilitate the design of apps for mobile devices (e.g., iPhone and Android devices).

In one embodiment, the IoT hub 110 manages a continuous bi-directional stream of data between the IoT devices 101-105 and the IoT service 120. In circumstances where updates to/from the IoT devices 101-105 are required in real time (e.g., where a user needs to view the current status of security devices or environmental readings), the IoT hub may maintain an open TCP socket to provide regular updates to the user device 135 and/or external Websites 130. The specific networking protocol used to provide updates may be tweaked based on the needs of the underlying application. For example, in some cases, where may not make sense to have a continuous bi-directional stream, a simple request/response protocol may be used to gather information when needed.

In one embodiment, both the IoT hub 110 and the IoT devices 101-105 are automatically upgradeable over the network. In particular, when a new update is available for the IoT hub 110 it may automatically download and install the update from the IoT service 120. It may first copy the updated code into a local memory, run and verify the update before swapping out the older program code. Similarly, when updates are available for each of the IoT devices 101-105, they may initially be downloaded by the IoT hub 110 and pushed out to each of the IoT devices 101-105. Each IoT device 101-105 may then apply the update in a similar manner as described above for the IoT hub and report back the results of the update to the IoT hub 110. If the update is successful, then the IoT hub 110 may delete the update from its memory and record the latest version of code installed on each IoT device (e.g., so that it may continue to check for new updates for each IoT device).

In one embodiment, the IoT hub 110 is powered via A/C power. In particular, the IoT hub 110 may include a power unit 390 with a transformer for transforming A/C voltage supplied via an A/C power cord to a lower DC voltage.

Figure 4A:
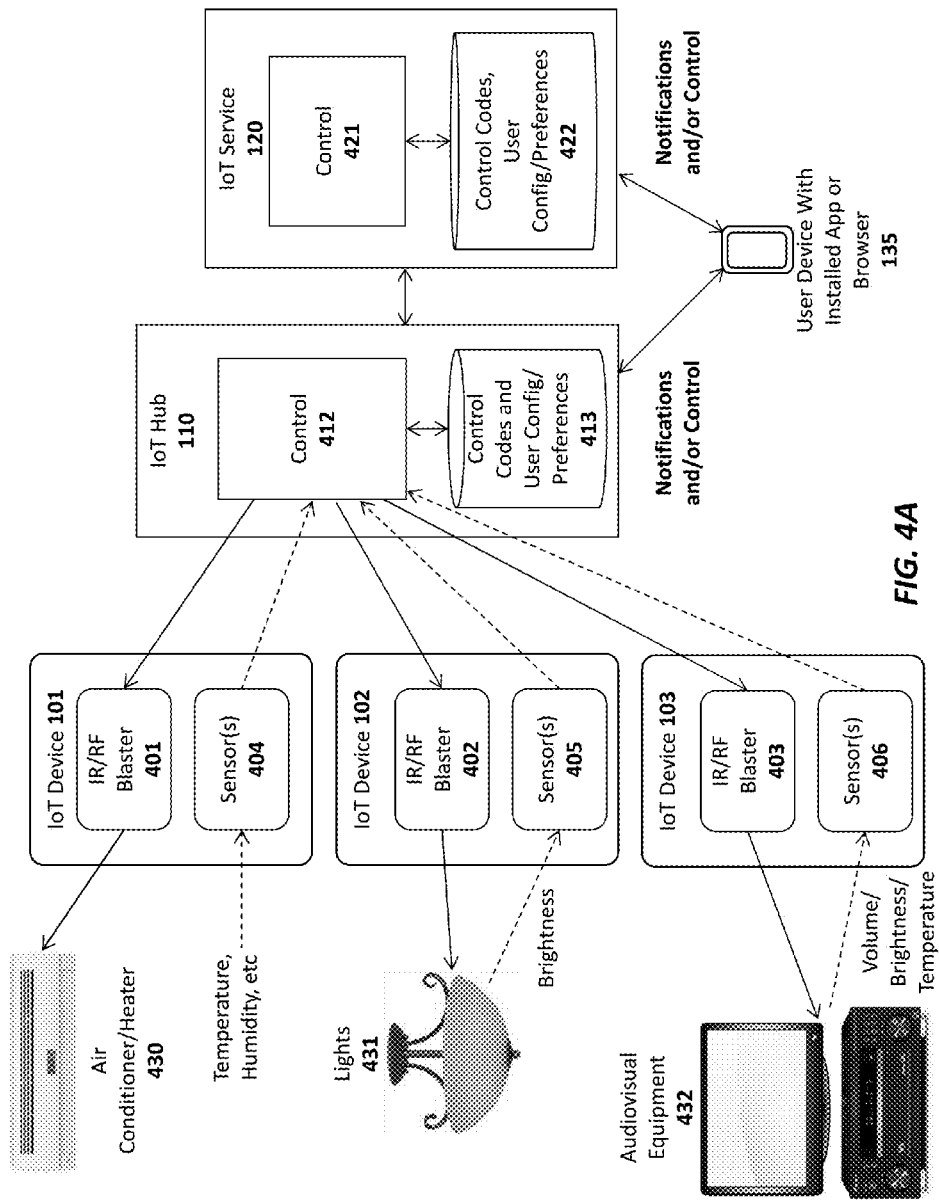
FIG. 4A-B illustrate embodiments of the invention for controlling and collecting data from IoT devices, and generating notifications.

FIG. 4A illustrates one embodiment of the invention for performing universal remote control operations using the IoT system. In particular, in this embodiment, a set of IoT devices 101-103 are equipped with infrared (IR) and/or radio frequency (RF) blasters 401-403, respectively, for transmitting remote control codes to control various different types of electronics equipment including air conditioners/heaters 430, lighting systems 431, and audiovisual equipment 432 (to name just a few). In the embodiment shown in FIG. 4A, the IoT devices 101-103 are also equipped with sensors 404-406, respectively, for detecting the operation of the devices which they control, as described below.

For example, sensor 404 in IoT device 101 may be a temperature and/or humidity sensor for sensing the current temperature/humidity and responsively controlling the air conditioner/heater 430 based on a current desired temperature. In this embodiment, the air conditioner/heater 430 is one which is designed to be controlled via a remote control device (typically a remote control which itself has a temperature sensor embedded therein). In one embodiment, the user provides the desired temperature to the IoT hub 110 via an app or browser installed on a user device 135. Control logic 412 executed on the IoT hub 110 receives the current temperature/humidity data from the sensor 404 and responsively transmits commands to the IoT device 101 to control the IR/RF blaster 401 in accordance with the desired temperature/humidity. For example, if the temperature is below the desired temperature, then the control logic 412 may transmit a command to the air conditioner/heater via the IR/RF blaster 401 to increase the temperature (e.g., either by turning off the air conditioner or turning on the heater). The command may include the necessary remote control code stored in a database 413 on the IoT hub 110. Alternatively, or in addition, the IoT service 421 may implement control logic 421 to control the electronics equipment 430-432 based on specified user preferences and stored control codes 422.

IoT device 102 in the illustrated example is used to control lighting 431. In particular, sensor 405 in IoT device 102 may photosensor or photodetector configured to detect the current brightness of the light being produced by a light fixture 431 (or other lighting apparatus). The user may specify a desired lighting level (including an indication of ON or OFF) to the IoT hub 110 via the user device 135. In response, the control logic 412 will transmit commands to the IR/RF blaster 402 to control the current brightness level of the lights 431 (e.g., increasing the lighting if the current brightness is too low or decreasing the lighting if the current brightness is too high; or simply turning the lights ON or OFF).

IoT device 103 in the illustrated example is configured to control audiovisual equipment 432 (e.g., a television, A/V receiver, cable/satellite receiver, AppleTV™, etc). Sensor 406 in IoT device 103 may be an audio sensor (e.g., a microphone and associated logic) for detecting a current ambient volume level and/or a photosensor to detect whether a television is on or off based on the light generated by the television (e.g., by measuring the light within a specified spectrum). Alternatively, sensor 406 may include a temperature sensor connected to the audiovisual equipment to detect whether the audio equipment is on or off based on the detected temperature. Once again, in response to user input via the user device 135, the control logic 412 may transmit commands to the audiovisual equipment via the IR blaster 403 of the IoT device 103.

It should be noted that the foregoing are merely illustrative examples of one embodiment of the invention. The underlying principles of the invention are not limited to any particular type of sensors or equipment to be controlled by IoT devices.

In an embodiment in which the IoT devices 101-103 are coupled to the IoT hub 110 via a Bluetooth LE connection, the sensor data and commands are sent over the Bluetooth LE channel. However, the underlying principles of the invention are not limited to Bluetooth LE or any other communication standard.

Figure 4B:
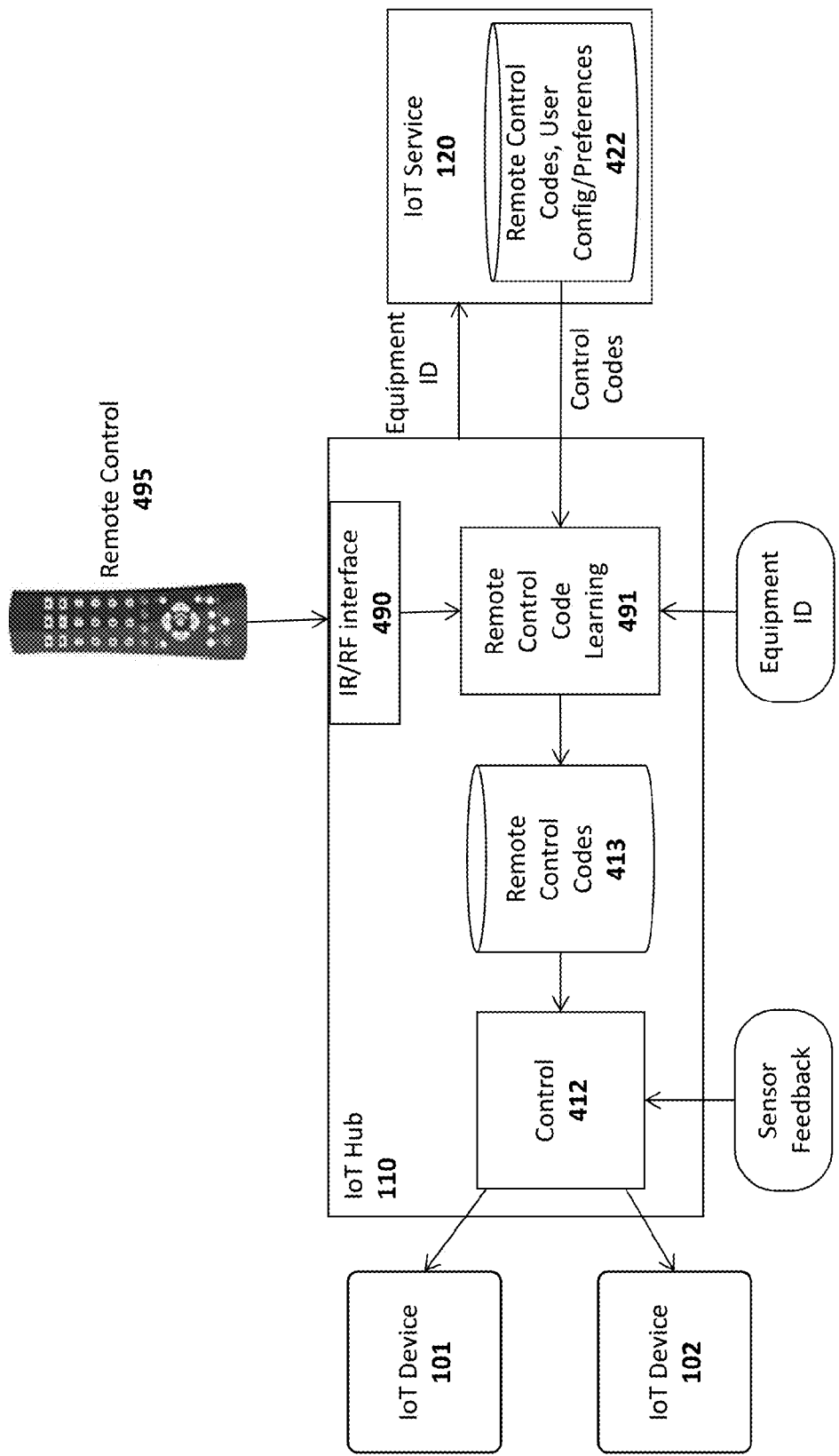

In one embodiment, the control codes required to control each of the pieces of electronics equipment are stored in a database 413 on the IoT hub 110 and/or a database 422 on the IoT service 120. As illustrated in FIG. 4B, the control codes may be provided to the IoT hub 110 from a master database of control codes 422 for different pieces of equipment maintained on the IoT service 120. The end user may specify the types of electronic (or other) equipment to be controlled via the app or browser executed on the user device 135 and, in response, a remote control code learning module 491 on the IoT hub may retrieve the required IR/RF codes from the remote control code database 492 on the IoT service 120 (e.g., identifying each piece of electronic equipment with a unique ID).

In addition, in one embodiment, the IoT hub 110 is equipped with an IR/RF interface 490 to allow the remote control code learning module 491 to "learn" new remote control codes directly from the original remote control 495 provided with the electronic equipment. For example, if control codes for the original remote control provided with the air conditioner 430 is not included in the remote control database, the user may interact with the IoT hub 110 via the app/browser on the user device 135 to teach the IoT hub 110 the various control codes generated by the original remote control (e.g., increase temperature, decrease temperature, etc). Once the remote control codes are learned they may be stored in the control code database 413 on the IoT hub 110 and/or sent back to the IoT service 120 to be included in the central remote control code database 492 (and subsequently used by other users with the same air conditioner unit 430).

In one embodiment, each of the IoT devices 101-103 have an extremely small form factor and may be affixed on or near their respective electronics equipment 430-432 using double-sided tape, a small nail, a magnetic attachment, etc. For control of a piece of equipment such as the air conditioner 430, it would be desirable to place the IoT device 101 sufficiently far away so that the sensor 404 can accurately measure the ambient temperature in the home (e.g., placing the IoT device directly on the air conditioner would result in a temperature measurement which would be too low when the air conditioner was running or too high when the heater was running). In contrast, the IoT device 102 used for controlling lighting may be placed on or near the lighting fixture 431 for the sensor 405 to detect the current lighting level.

In addition to providing general control functions as described, one embodiment of the IoT hub 110 and/or IoT service 120 transmits notifications to the end user related to the current status of each piece of electronics equipment. The notifications, which may be text messages and/or app-specific notifications, may then be displayed on the display of the user's mobile device 135. For example, if the user's air conditioner has been on for an extended period of time but the temperature has not changed, the IoT hub 110 and/or IoT service 120 may send the user a notification that the air conditioner is not functioning properly. If the user is not home (which may be detected via motion sensors or based on the user's current detected location), and the sensors 406 indicate that audiovisual equipment 430 is on or sensors 405 indicate that the lights are on, then a notification may be sent to the user, asking if the user would like to turn off the audiovisual equipment 432 and/or lights 431. The same type of notification may be sent for any equipment type.

Once the user receives a notification, he/she may remotely control the electronics equipment 430-432 via the app or browser on the user device 135. In one embodiment, the user device 135 is a touchscreen device and the app or browser displays an image of a remote control with user-selectable buttons for controlling the equipment 430-432. Upon receiving a notification, the user may open the graphical remote control and turn off or adjust the various different pieces of equipment. If connected via the IoT service 120, the user's selections may be forwarded from the IoT service 120 to the IoT hub 110 which will then control the equipment via the control logic 412. Alternatively, the user input may be sent directly to the IoT hub 110 from the user device 135.

In one embodiment, the user may program the control logic 412 on the IoT hub 110 to perform various automatic control functions with respect to the electronics equipment 430-432. In addition to maintaining a desired temperature, brightness level, and volume level as described above, the control logic 412 may automatically turn off the electronics equipment if certain conditions are detected. For example, if the control logic 412 detects that the user is not home and that the air conditioner is not functioning, it may automatically turn off the air conditioner. Similarly, if the user is not home, and the sensors 406 indicate that audiovisual equipment 430 is on or sensors 405 indicate that the lights are on, then the control logic 412 may automatically transmit commands via the IR/RF blasters 403 and 402, to turn off the audiovisual equipment and lights, respectively.

Figure 5:
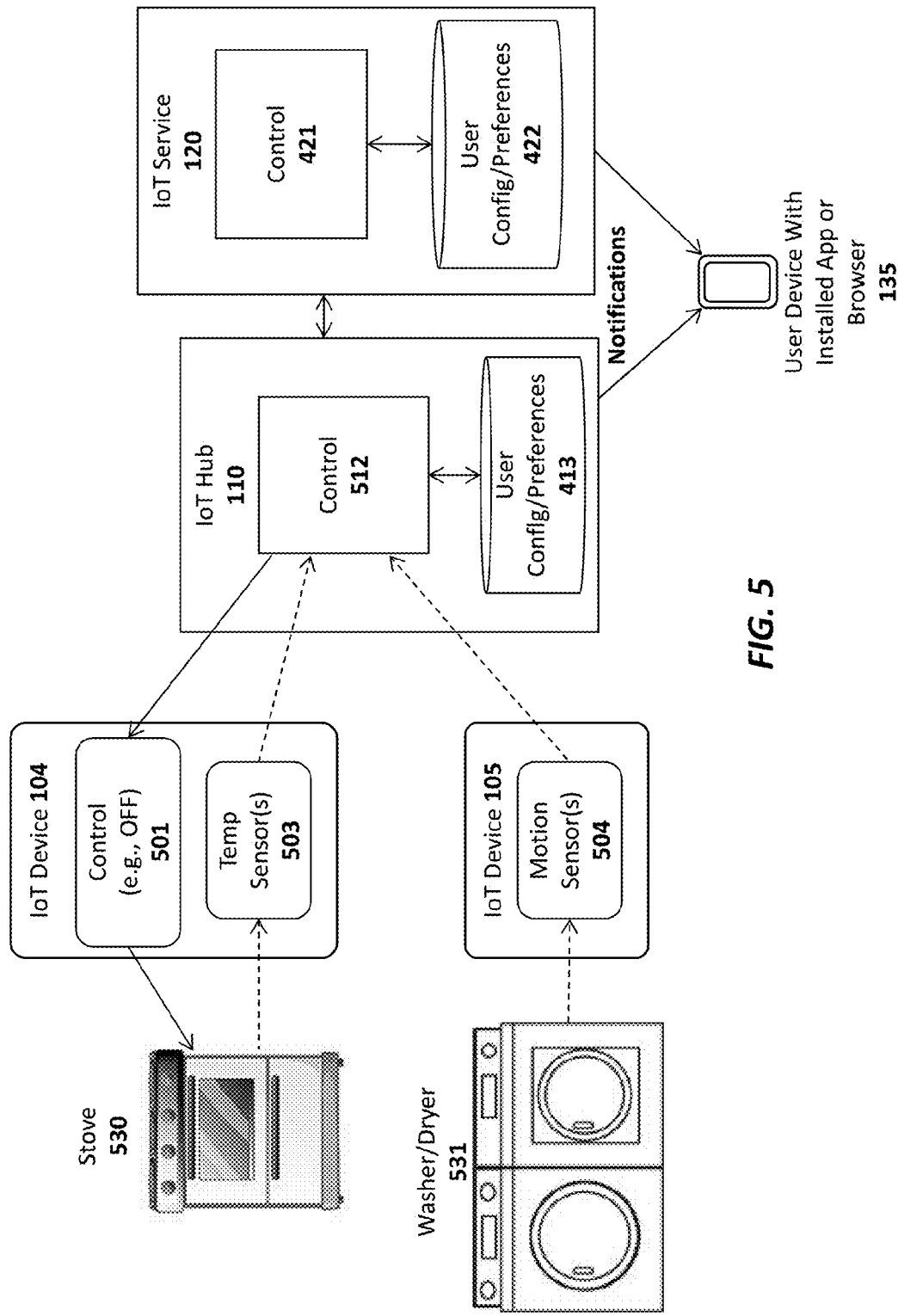
FIG. 5 illustrates embodiments of the invention for collecting data from IoT devices and generating notifications from an IoT hub and/or IoT service.

FIG. 5 illustrates additional embodiments of IoT devices 104-105 equipped with sensors 503-504 for monitoring electronic equipment 530-531. In particular, the IoT device 104 of this embodiment includes a temperature sensor 503 which may be placed on or near a stove 530 to detect when the stove has been left on. In one embodiment, the IoT device 104 transmits the current temperature measured by the temperature sensor 503 to the IoT hub 110 and/or the IoT service 120. If the stove is detected to be on for more than a threshold time period (e.g., based on the measured temperature), then control logic 512 may transmit a notification to the end user's device 135 informing the user that the stove 530 is on. In addition, in one embodiment, the IoT device 104 may include a control module 501 to turn off the stove, either in response to receiving an instruction from the user or automatically (if the control logic 512 is programmed to do so by the user). In one embodiment, the control logic 501 comprises a switch to cut off electricity or gas to the stove 530. However, in other embodiments, the control logic 501 may be integrated within the stove itself.

FIG. 5 also illustrates an IoT device 105 with a motion sensor 504 for detecting the motion of certain types of electronics equipment such as a washer and/or dryer. Another sensor that may be used is an audio sensor (e.g., microphone and logic) for detecting an ambient volume level. As with the other embodiments described above, this embodiment may transmit notifications to the end user if certain specified conditions are met (e.g., if motion is detected for an extended period of time, indicating that the washer/dryer are not turning off). Although not shown in FIG. 5, IoT device 105 may also be equipped with a control module to turn off the washer/dryer 531 (e.g., by switching off electric/gas), automatically, and/or in response to user input.

In one embodiment, a first IoT device with control logic and a switch may be configured to turn off all power in the user's home and a second IoT device with control logic and a switch may be configured to turn off all gas in the user's home. IoT devices with sensors may then be positioned on or near electronic or gas-powered equipment in the user's home. If the user is notified that a particular piece of equipment has been left on (e.g., the stove 530), the user may then send a command to turn off all electricity or gas in the home to prevent damage. Alternatively, the control logic 512 in the IoT hub 110 and/or the IoT service 120 may be configured to automatically turn off electricity or gas in such situations.

In one embodiment, the IoT hub 110 and IoT service 120 communicate at periodic intervals. If the IoT service 120 detects that the connection to the IoT hub 110 has been lost (e.g., by failing to receive a request or response from the IoT hub for a specified duration), it will communicate this information to the end user's device 135 (e.g., by sending a text message or app-specific notification).

Embodiments for Improved Security

In one embodiment, the low power microcontroller 200 of each IoT device 101 and the low power logic/microcontroller 301 of the IoT hub 110 include a secure key store for storing encryption keys used by the embodiments described below (see, e.g., FIGS. 6-11 and associated text). Alternatively, the keys may be secured in a subscriber identify module (SIM) as discussed below.

Figure 6:
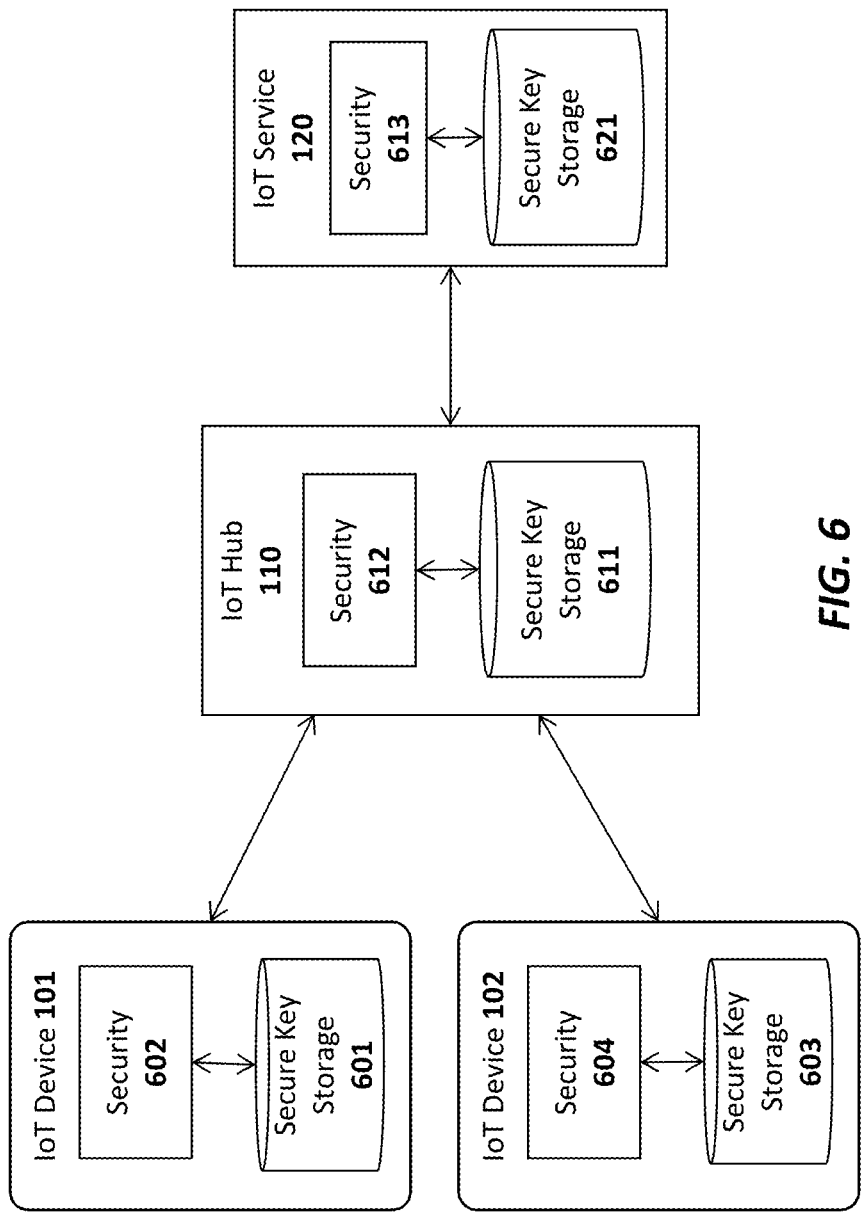
FIG. 6 illustrates embodiments of the invention which implements improved security techniques such as encryption and digital signatures.

FIG. 6 illustrates a high level architecture which uses public key infrastructure (PKI) techniques and/or symmetric key exchange/encryption techniques to encrypt communications between the IoT Service 120, the IoT hub 110 and the IoT devices 101-102.

Embodiments which use public/private key pairs will first be described, followed by embodiments which use symmetric key exchange/encryption techniques. In particular, in an embodiment which uses PKI, a unique public/private key pair is associated with each IoT device 101-102, each IoT hub 110 and the IoT service 120. In one embodiment, when a new IoT hub 110 is set up, its public key is provided to the IoT service 120 and when a new IoT device 101 is set up, it's public key is provided to both the IoT hub 110 and the IoT service 120. Various techniques for securely exchanging the public keys between devices are described below. In one embodiment, all public keys are signed by a master key known to all of the receiving devices (i.e., a form of certificate) so that any receiving device can verify the validity of the public keys by validating the signatures. Thus, these certificates would be exchanged rather than merely exchanging the raw public keys.

As illustrated, in one embodiment, each IoT device 101, 102 includes a secure key storage 601, 603, respectively, for security storing each device's private key. Security logic 602, 1304 then utilizes the securely stored private keys to perform the encryption/decryption operations described herein. Similarly, the IoT hub 110 includes a secure storage 611 for storing the IoT hub private key and the public keys of the IoT devices 101-102 and the IoT service 120; as well as security logic 612 for using the keys to perform encryption/decryption operations. Finally, the IoT service 120 may include a secure storage 621 for security storing its own private key, the public keys of various IoT devices and IoT hubs, and a security logic 613 for using the keys to encrypt/decrypt communication with IoT hubs and devices. In one embodiment, when the IoT hub 110 receives a public key certificate from an IoT device it can verify it (e.g., by validating the signature using the master key as described above), and then extract the public key from within it and store that public key in it's secure key store 611.

By way of example, in one embodiment, when the IoT service 120 needs to transmit a command or data to an IoT device 101 (e.g., a command to unlock a door, a request to read a sensor, data to be processed/displayed by the IoT device, etc) the security logic 613 encrypts the data/command using the public key of the IoT device 101 to generate an encrypted IoT device packet. In one embodiment, it then encrypts the IoT device packet using the public key of the IoT hub 110 to generate an IoT hub packet and transmits the IoT hub packet to the IoT hub 110. In one embodiment, the service 120 signs the encrypted message with it's private key or the master key mentioned above so that the device 101 can verify it is receiving an unaltered message from a trusted source. The device 101 may then validate the signature using the public key corresponding to the private key and/or the master key. As mentioned above, symmetric key exchange/encryption techniques may be used instead of public/private key encryption. In these embodiments, rather than privately storing one key and providing a corresponding public key to other devices, the devices may each be provided with a copy of the same symmetric key to be used for encryption and to validate signatures. One example of a symmetric key algorithm is the Advanced Encryption Standard (AES), although the underlying principles of the invention are not limited to any type of specific symmetric keys.

Using a symmetric key implementation, each device 101 enters into a secure key exchange protocol to exchange a symmetric key with the IoT hub 110. A secure key provisioning protocol such as the Dynamic Symmetric Key Provisioning Protocol (DSKPP) may be used to exchange the keys over a secure communication channel (see, e.g., Request for Comments (RFC) 6063). However, the underlying principles of the invention are not limited to any particular key provisioning protocol.

Once the symmetric keys have been exchanged, they may be used by each device 101 and the IoT hub 110 to encrypt communications. Similarly, the IoT hub 110 and IoT service 120 may perform a secure symmetric key exchange and then use the exchanged symmetric keys to encrypt communications. In one embodiment a new symmetric key is exchanged periodically between the devices 101 and the hub 110 and between the hub 110 and the IoT service 120. In one embodiment, a new symmetric key is exchanged with each new communication session between the devices 101, the hub 110, and the service 120 (e.g., a new key is generated and securely exchanged for each communication session). In one embodiment, if the security module 612 in the IoT hub is trusted, the service 120 could negotiate a session key with the hub security module 1312 and then the security module 612 would negotiate a session key with each device 120. Messages from the service 120 would then be decrypted and verified in the hub security module 612 before being re-encrypted for transmission to the device 101.

In one embodiment, to prevent a compromise on the hub security module 612 a one-time (permanent) installation key may be negotiated between the device 101 and service 120 at installation time. When sending a message to a device 101 the service 120 could first encrypt/MAC with this device installation key, then encrypt/MAC that with the hub's session key. The hub 110 would then verify and extract the encrypted device blob and send that to the device.

In one embodiment of the invention, a counter mechanism is implemented to prevent replay attacks. For example, each successive communication from the device 101 to the hub 110 (or vice versa) may be assigned a continually increasing counter value. Both the hub 110 and device 101 will track this value and verify that the value is correct in each successive communication between the devices. The same techniques may be implemented between the hub 110 and the service 120. Using a counter in this manner would make it more difficult to spoof the communication between each of the devices (because the counter value would be incorrect). However, even without this a shared installation key between the service and device would prevent network (hub) wide attacks to all devices.

In one embodiment, when using public/private key encryption, the IoT hub 110 uses its private key to decrypt the IoT hub packet and generate the encrypted IoT device packet, which it transmits to the associated IoT device 101. The IoT device 101 then uses its private key to decrypt the IoT device packet to generate the command/data originated from the IoT service 120. It may then process the data and/or execute the command. Using symmetric encryption, each device would encrypt and decrypt with the shared symmetric key. If either case, each transmitting device may also sign the message with it's private key so that the receiving device can verify it's authenticity.

A different set of keys may be used to encrypt communication from the IoT device 101 to the IoT hub 110 and to the IoT service 120. For example, using a public/private key arrangement, in one embodiment, the security logic 602 on the IoT device 101 uses the public key of the IoT hub 110 to encrypt data packets sent to the IoT hub 110. The security logic 612 on the IoT hub 110 may then decrypt the data packets using the IoT hub's private key. Similarly, the security logic 602 on the IoT device 101 and/or the security logic 612 on the IoT hub 110 may encrypt data packets sent to the IoT service 120 using the public key of the IoT service 120 (which may then be decrypted by the security logic 613 on the IoT service 120 using the service's private key). Using symmetric keys, the device 101 and hub 110 may share a symmetric key while the hub and service 120 may share a different symmetric key.

While certain specific details are set forth above in the description above, it should be noted that the underlying principles of the invention may be implemented using various different encryption techniques. For example, while some embodiments discussed above use asymmetric public/private key pairs, an alternate embodiment may use symmetric keys securely exchanged between the various IoT devices 101-102, IoT hubs 110, and the IoT service 120. Moreover, in some embodiments, the data/command itself is not encrypted, but a key is used to generate a signature over the data/command (or other data structure). The recipient may then use its key to validate the signature.

Figure 7:
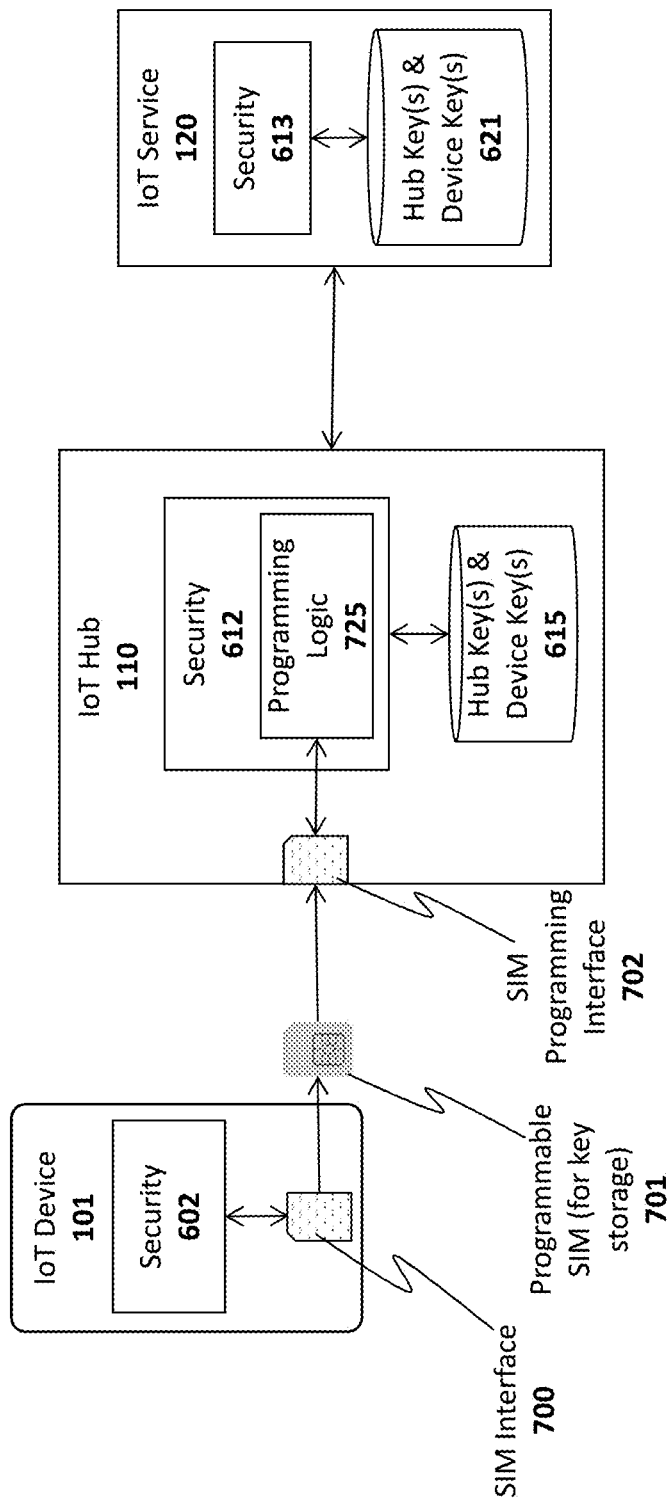
FIG. 7 illustrates one embodiment of an architecture in which a subscriber identity module (SIM) is used to store keys on IoT devices.

As illustrated in FIG. 7, in one embodiment, the secure key storage on each IoT device 101 is implemented using a programmable subscriber identity module (SIM) 701. In this embodiment, the IoT device 101 may initially be provided to the end user with an un-programmed SIM card 701 seated within a SIM interface 700 on the IoT device 101. In order to program the SIM with a set of one or more encryption keys, the user takes the programmable SIM card 701 out of the SIM interface 500 and inserts it into a SIM programming interface 702 on the IoT hub 110. Programming logic 725 on the IoT hub then securely programs the SIM card 701 to register/pair the IoT device 101 with the IoT hub 110 and IoT service 120. In one embodiment, a public/private key pair may be randomly generated by the programming logic 725 and the public key of the pair may then be stored in the IoT hub's secure storage device 411 while the private key may be stored within the programmable SIM 701. In addition, the programming logic 525 may store the public keys of the IoT hub 110, the IoT service 120, and/or any other IoT devices 101 on the SIM card 601 (to be used by the security logic 1302 on the IoT device 101 to encrypt outgoing data). Once the SIM 701 is programmed, the new IoT device 101 may be provisioned with the IoT Service 120 using the SIM as a secure identifier (e.g., using existing techniques for registering a device using a SIM). Following provisioning, both the IoT hub 110 and the IoT service 120 will securely store a copy of the IoT device's public key to be used when encrypting communication with the IoT device 101.

The techniques described above with respect to FIG. 7 provide enormous flexibility when providing new IoT devices to end users. Rather than requiring a user to directly register each SIM with a particular service provider upon sale/purchase (as is currently done), the SIM may be programmed directly by the end user via the IoT hub 110 and the results of the programming may be securely communicated to the IoT service 120. Consequently, new IoT devices 101 may be sold to end users from online or local retailers and later securely provisioned with the IoT service 120.

While the registration and encryption techniques are described above within the specific context of a SIM (Subscriber Identity Module), the underlying principles of the invention are not limited to a "SIM" device. Rather, the underlying principles of the invention may be implemented using any type of device having secure storage for storing a set of encryption keys. Moreover, while the embodiments above include a removable SIM device, in one embodiment, the SIM device is not removable but the IoT device itself may be inserted within the programming interface 702 of the IoT hub 110.

In one embodiment, rather than requiring the user to program the SIM (or other device), the SIM is pre-programmed into the IoT device 101, prior to distribution to the end user. In this embodiment, when the user sets up the IoT device 101, various techniques described herein may be used to securely exchange encryption keys between the IoT hub 110/IoT service 120 and the new IoT device 101.

Figure 8A:
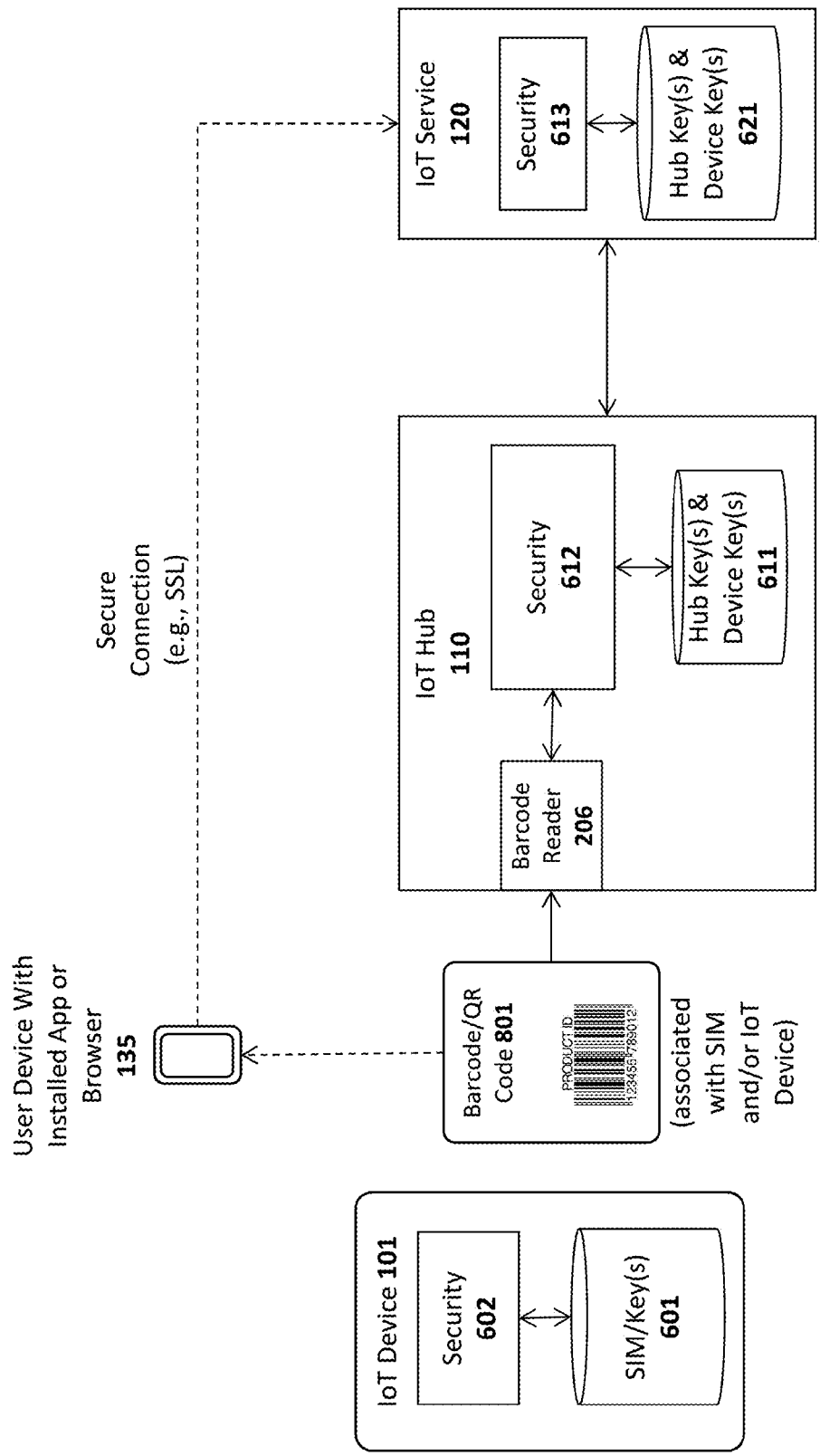
FIG. 8A illustrates one embodiment in which IoT devices are registered using barcodes or QR codes.

For example, as illustrated in FIG. 8A each IoT device 101 or SIM 401 may be packaged with a barcode or QR code 701 uniquely identifying the IoT device 101 and/or SIM 701. In one embodiment, the barcode or QR code 801 comprises an encoded representation of the public key for the IoT device 101 or SIM 1001. Alternatively, the barcode or QR code 801 may be used by the IoT hub 110 and/or IoT service 120 to identify or generate the public key (e.g., used as a pointer to the public key which is already stored in secure storage). The barcode or QR code 601 may be printed on a separate card (as shown in FIG. 8A) or may be printed directly on the IoT device itself. Regardless of where the barcode is printed, in one embodiment, the IoT hub 110 is equipped with a barcode reader 206 for reading the barcode and providing the resulting data to the security logic 1012 on the IoT hub 110 and/or the security logic 1013 on the IoT service 120. The security logic 1012 on the IoT hub 110 may then store the public key for the IoT device within its secure key storage 1011 and the security logic 1013 on the IoT service 120 may store the public key within its secure storage 1021 (to be used for subsequent encrypted communication).

In one embodiment, the data contained in the barcode or QR code 801 may also be captured via a user device 135 (e.g., such as an iPhone or Android device) with an installed IoT app or browser-based applet designed by the IoT service provider. Once captured, the barcode data may be securely communicated to the IoT service 120 over a secure connection (e.g., such as a secure sockets layer (SSL) connection). The barcode data may also be provided from the client device 135 to the IoT hub 110 over a secure local connection (e.g., over a local WiFi or Bluetooth LE connection).

The security logic 1002 on the IoT device 101 and the security logic 1012 on the IoT hub 110 may be implemented using hardware, software, firmware or any combination thereof. For example, in one embodiment, the security logic 1002, 1012 is implemented within the chips used for establishing the local communication channel 130 between the IoT device 101 and the IoT hub 110 (e.g., the Bluetooth LE chip if the local channel 130 is Bluetooth LE). Regardless of the specific location of the security logic 1002, 1012, in one embodiment, the security logic 1002, 1012 is designed to establish a secure execution environment for executing certain types of program code. This may be implemented, for example, by using TrustZone technology (available on some ARM processors) and/or Trusted Execution Technology (designed by Intel). Of course, the underlying principles of the invention are not limited to any particular type of secure execution technology.

In one embodiment, the barcode or QR code 701 may be used to pair each IoT device 101 with the IoT hub 110. For example, rather than using the standard wireless pairing process currently used to pair Bluetooth LE devices, a pairing code embedded within the barcode or QR code 701 may be provided to the IoT hub 110 to pair the IoT hub with the corresponding IoT device.

Figure 8B:
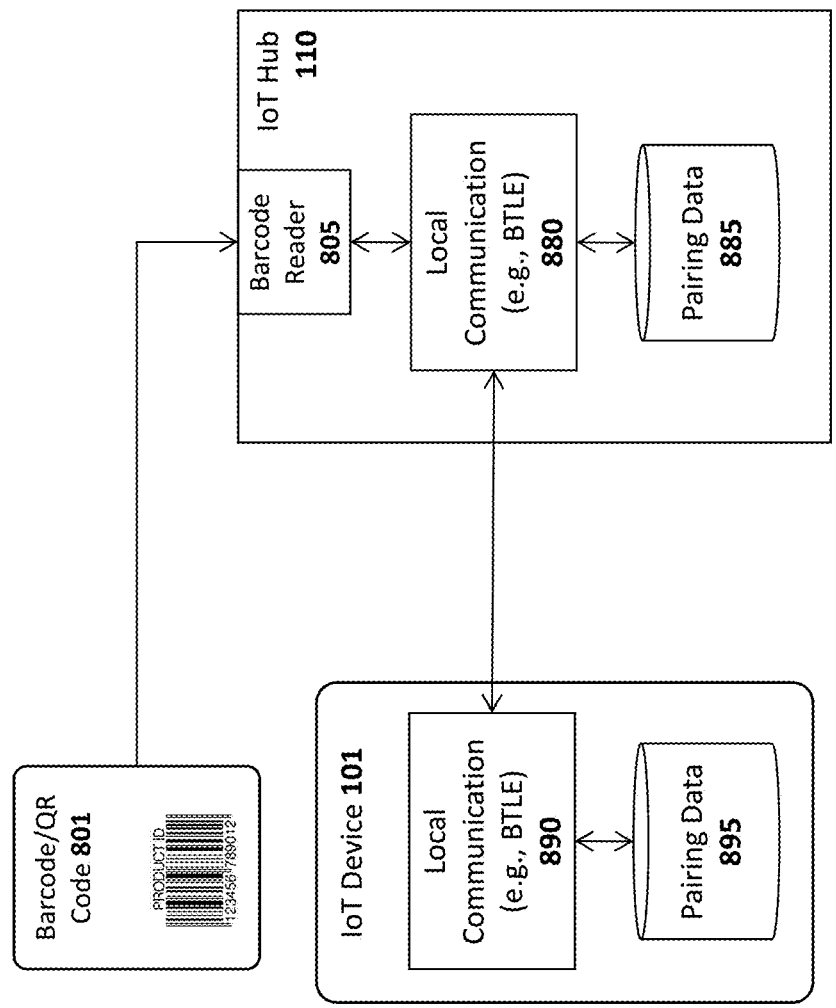
FIG. 8B illustrates one embodiment in which pairing is performed using barcodes or QR codes.

FIG. 8B illustrates one embodiment in which the barcode reader 206 on the IoT hub 110 captures the barcode/QR code 801 associated with the IoT device 101. As mentioned, the barcode/QR code 801 may be printed directly on the IoT device 101 or may be printed on a separate card provided with the IoT device 101. In either case, the barcode reader 206 reads the pairing code from the barcode/QR code 801 and provides the pairing code to the local communication module 880. In one embodiment, the local communication module 880 is a Bluetooth LE chip and associated software, although the underlying principles of the invention are not limited to any particular protocol standard. Once the pairing code is received, it is stored in a secure storage containing pairing data 885 and the IoT device 101 and IoT hub 110 are automatically paired. Each time the IoT hub is paired with a new IoT device in this manner, the pairing data for that pairing is stored within the secure storage 685. In one embodiment, once the local communication module 880 of the IoT hub 110 receives the pairing code, it may use the code as a key to encrypt communications over the local wireless channel with the IoT device 101.

Similarly, on the IoT device 101 side, the local communication module 890 stores pairing data within a local secure storage device 895 indicating the pairing with the IoT hub. The pairing data 895 may include the pre-programmed pairing code identified in the barcode/QR code 801. The pairing data 895 may also include pairing data received from the local communication module 880 on the IoT hub 110 required for establishing a secure local communication channel (e.g., an additional key to encrypt communication with the IoT hub 110).

Thus, the barcode/QR code 801 may be used to perform local pairing in a far more secure manner than current wireless pairing protocols because the pairing code is not transmitted over the air. In addition, in one embodiment, the same barcode/QR code 801 used for pairing may be used to identify encryption keys to build a secure connection from the IoT device 101 to the IoT hub 110 and from the IoT hub 110 to the IoT service 120.

A method for programming a SIM card in accordance with one embodiment of the invention is illustrated in FIG. 9. The method may be implemented within the system architecture described above, but is not limited to any particular system architecture.

At 901, a user receives a new IoT device with a blank SIM card and, at 802, the user inserts the blank SIM card into an IoT hub. At 903, the user programs the blank SIM card with a set of one or more encryption keys. For example, as mentioned above, in one embodiment, the IoT hub may randomly generate a public/private key pair and store the private key on the SIM card and the public key in its local secure storage. In addition, at 904, at least the public key is transmitted to the IoT service so that it may be used to identify the IoT device and establish encrypted communication with the IoT device. As mentioned above, in one embodiment, a programmable device other than a "SIM" card may be used to perform the same functions as the SIM card in the method shown in FIG. 9.

Figure 10:
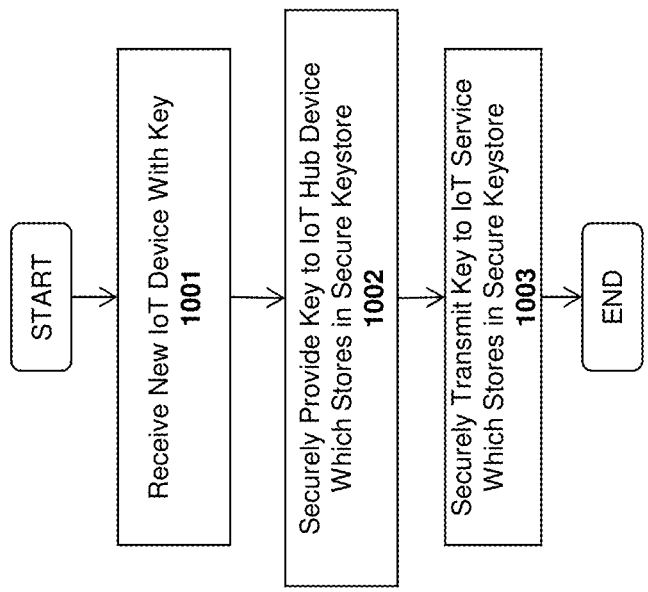
FIG. 10 illustrates one embodiment of a method for registering an IoT device with an IoT hub and IoT service.

A method for integrating a new IoT device into a network is illustrated in FIG. 10. The method may be implemented within the system architecture described above, but is not limited to any particular system architecture.

At 1001, a user receives a new IoT device to which an encryption key has been pre-assigned. At 1002, the key is securely provided to the IoT hub. As mentioned above, in one embodiment, this involves reading a barcode associated with the IoT device to identify the public key of a public/private key pair assigned to the device. The barcode may be read directly by the IoT hub or captured via a mobile device via an app or bowser. In an alternate embodiment, a secure communication channel such as a Bluetooth LE channel, a near field communication (NFC) channel or a secure WiFi channel may be established between the IoT device and the IoT hub to exchange the key. Regardless of how the key is transmitted, once received, it is stored in the secure keystore of the IoT hub device. As mentioned above, various secure execution technologies may be used on the IoT hub to store and protect the key such as Secure Enclaves, Trusted Execution Technology (TXT), and/or Trustzone. In addition, at 1003, the key is securely transmitted to the IoT service which stores the key in its own secure keystore. It may then use the key to encrypt communication with the IoT device. One again, the exchange may be implemented using a certificate/signed key. Within the hub 110 it is particularly important to prevent modification/addition/removal of the stored keys.

Figure 11:
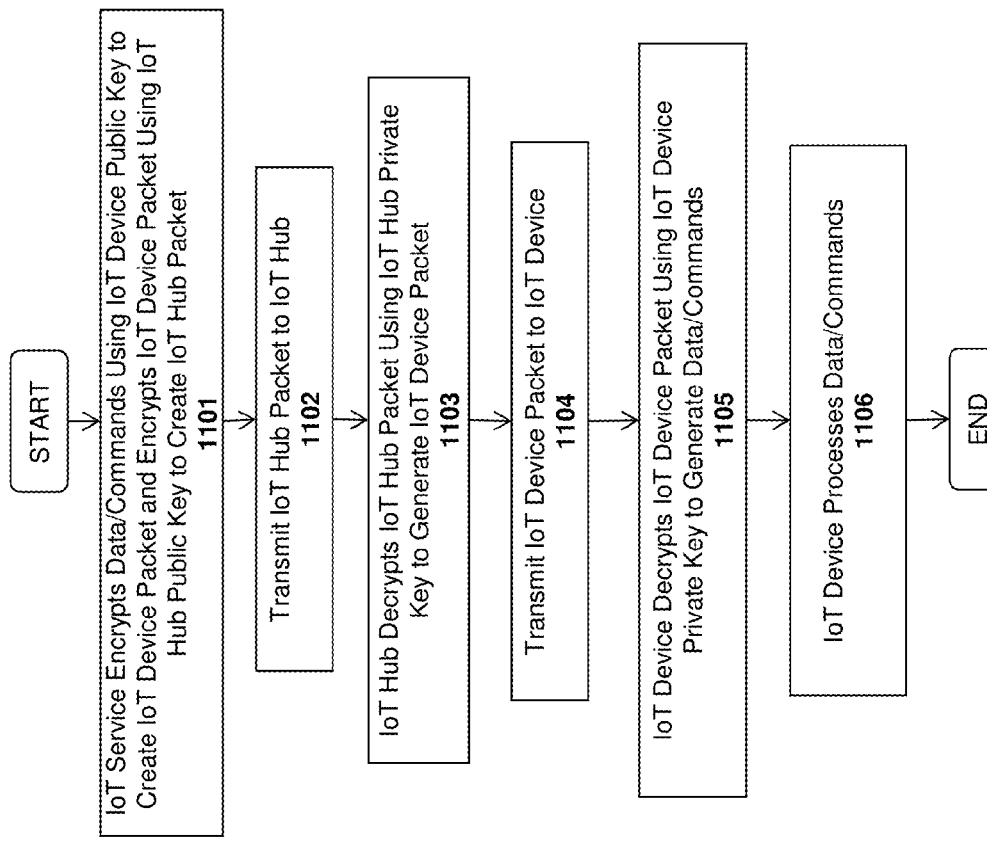
FIG. 11 illustrates one embodiment of a method for encrypting data to be transmitted to an IoT device.

A method for securely communicating commands/data to an IoT device using public/private keys is illustrated in FIG. 11. The method may be implemented within the system architecture described above, but is not limited to any particular system architecture.

At 1101, the IoT service encrypts the data/commands using the IoT device public key to create an IoT device packet. It then encrypts the IoT device packet using IoT hub's public key to create the IoT hub packet (e.g., creating an IoT hub wrapper around the IoT device packet). At 1102, the IoT service transmits the IoT hub packet to the IoT hub. At 1103, the IoT hub decrypts the IoT hub packet using the IoT hub's private key to generate the IoT device packet. At 1104 it then transmits the IoT device packet to the IoT device which, at 1105, decrypts the IoT device packet using the IoT device private key to generate the data/commands. At 1106, the IoT device processes the data/commands.

In an embodiment which uses symmetric keys, a symmetric key exchange may be negotiated between each of the devices (e.g., each device and the hub and between the hub and the service). Once the key exchange is complete, each transmitting device encrypts and/or signs each transmission using the symmetric key before transmitting data to the receiving device.

System and Method for an Internet of Things (IoT) Moisture Sensor

Figure 12:
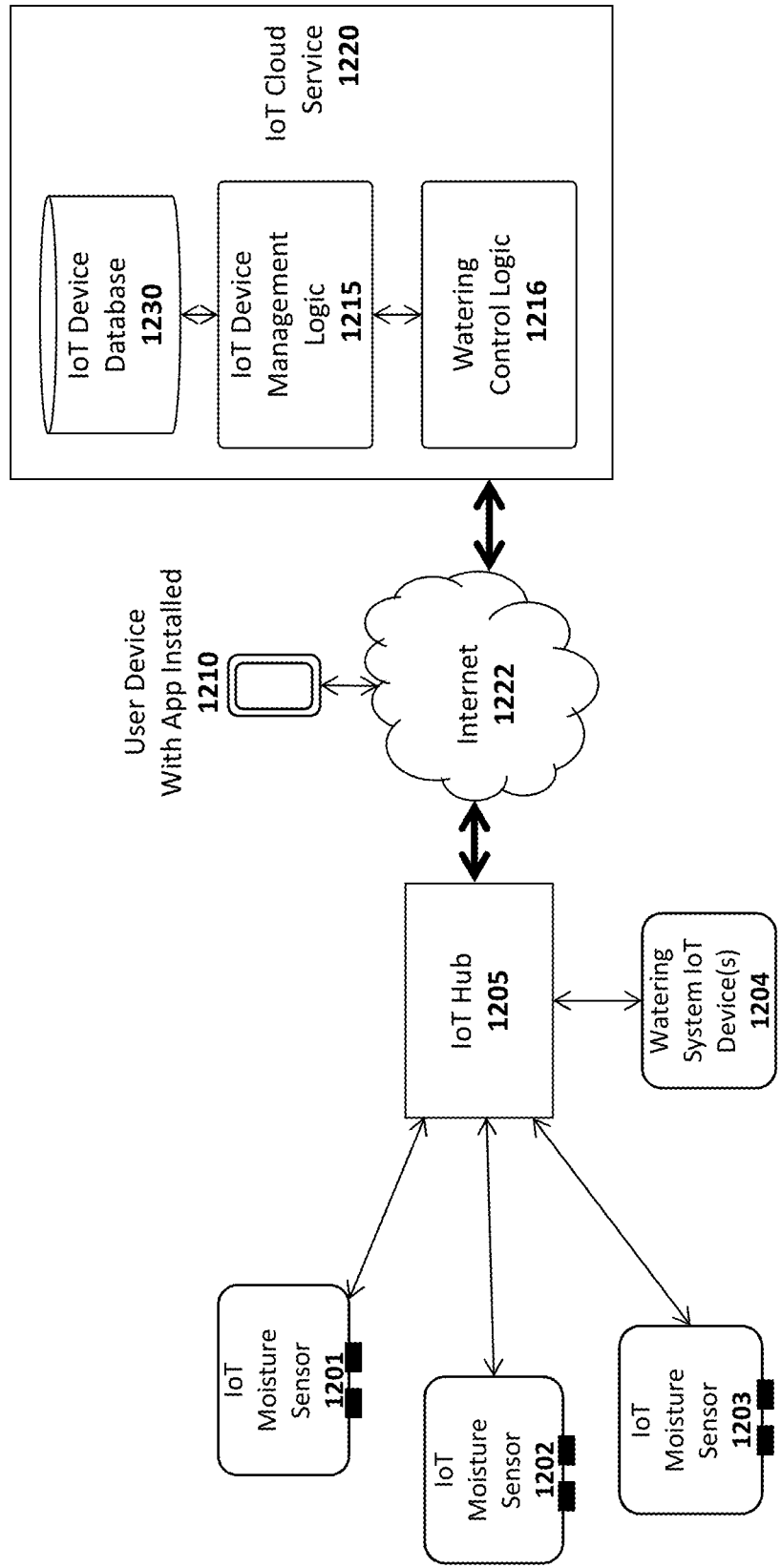
FIG. 12 illustrates a system architecture in accordance with one embodiment of the invention.
Figure 13:
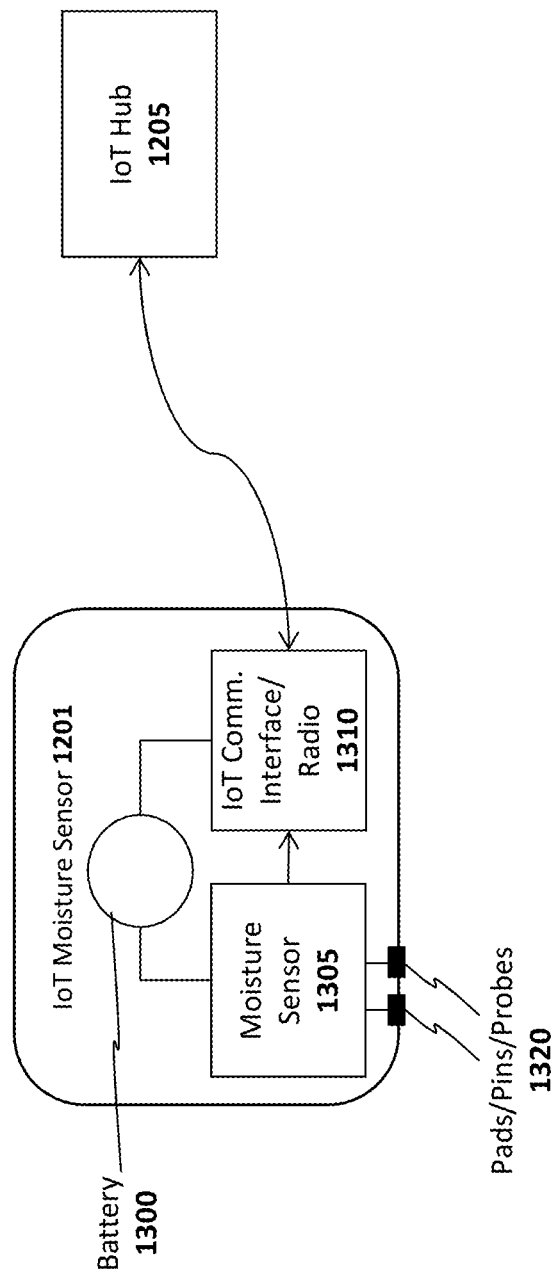
FIG. 13 illustrates an IoT moisture sensor in accordance with one embodiment of the invention.
Figure 14B:
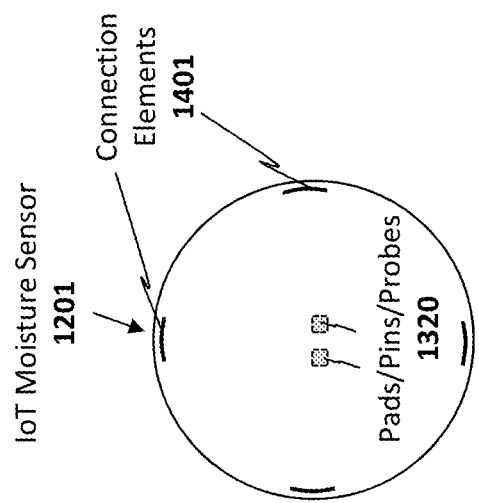
FIGS. 14A-B illustrates a form factor for one embodiment of the IoT moisture sensor.
Figure 14A:
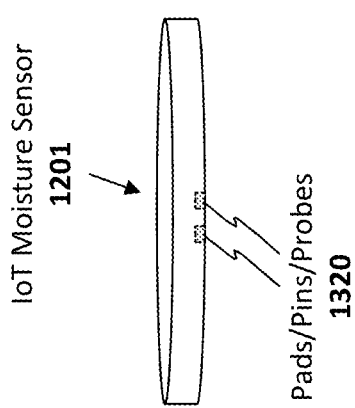
Figure 15:
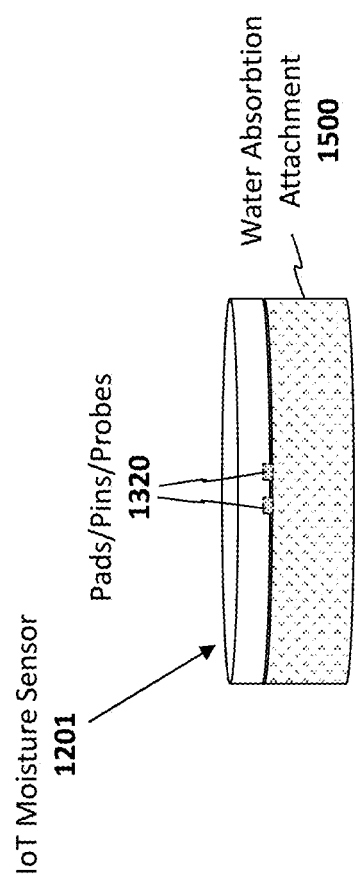
FIG. 15 illustrates an IoT moisture sensor with an exemplary water absorption attachment such as a sponge.
Figure 16:
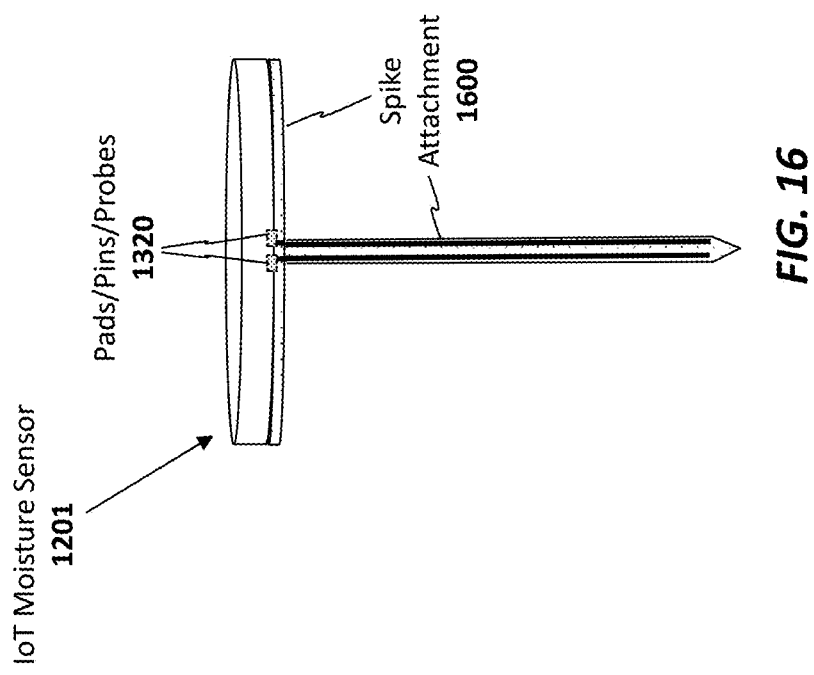
FIG. 16 illustrates an IoT moisture sensor with an exemplary spike attachment.
Figure 17:
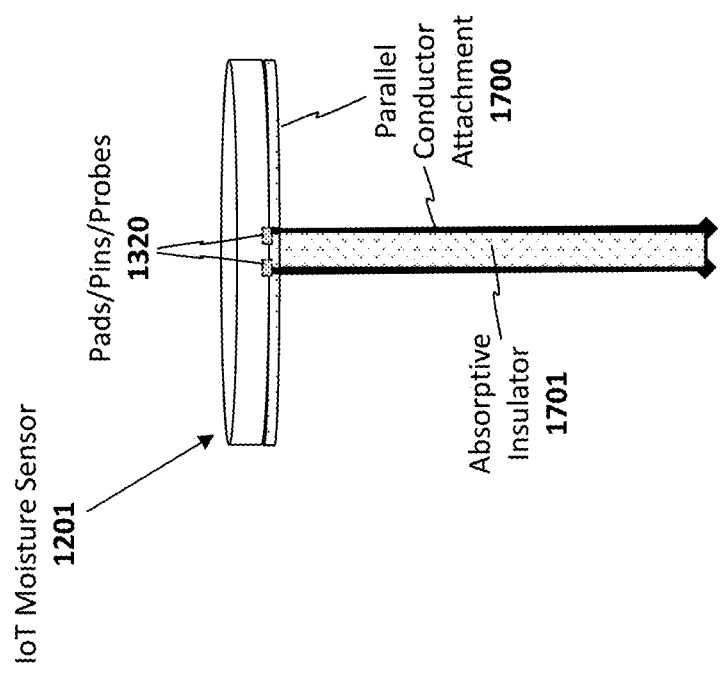
FIG. 17 illustrates an IoT moisture sensor with an exemplary parallel conductor attachment.

One embodiment of the invention comprises an Internet of Things (IoT) moisture sensor which may be coupled to an IoT system to provide moisture readings and/or control watering. FIG. 12, for example, illustrates a system architecture with three such IoT moisture sensor devices 1201-1203 which may be used for various moisture detection applications. For example, in one embodiment, one or more of the IoT moisture sensor devices 1201-1203 may be placed into the soil (e.g., near grassy areas, bushes, flowers, etc) and report back the current moisture level to the IoT cloud service 1220 via the IoT hub 1205. The user may then log in via the user device 1210 via an app or application to view the moisture levels. In addition, in one embodiment, one or more watering system IoT devices 1204 may be configured to turn on/off the various sprinklers and slow drip watering devices in response to the moisture data provided by the IoT moisture sensors 1201-1203. For example, in one embodiment, when the moisture level of a particular moisture sensor 1201 reaches a user-specified threshold, watering control logic 1216 on the IoT cloud service 1220 may transmit a command to turn on the sprinkler or other watering device supplying water to the area measured by the IoT moisture sensor 1201. While shown in the IoT cloud service 1220 for the purpose of explanation, the watering control logic 1216 may also be implemented on the IoT hub 1205 or directly within the watering system IoT devices 1204.

The interaction between the various system components shown in FIG. 12 may occur as described above. For example, the IoT hub 1205 communicates with the IoT devices 1201-1203 over low power wireless communication channels such as Bluetooth Low Energy (BTLE) channels and, in one embodiment, establishes a communication channel with the IoT cloud service 1220.

As illustrated, the IoT cloud service 1220 may include an IoT device database 1230 comprising database records for each of the IoT devices 1201-1204 and IoT hubs 1205 configured in the system (which may include a plurality of IoT hubs and devices not shown in FIG. 12). IoT device management logic 1215 creates the database records for new IoT devices and updates the IoT device records in response to data transmitted by each of the IoT devices 1201-1204.

The IoT device management logic 1215 may also implement the various security/encryption functions described above to add new devices to the system (e.g., using QR codes/barcodes) and use keys to encrypt communications and/or generate digital signatures when communicating with the IoT devices 1201-1204. In one embodiment, a user may access information related to each of the IoT devices 1201-1204 and/or control the devices via an app installed on a user device 1210 which may be a smartphone device such as an Android® device or iPhone®. In addition, the user may access and control the IoT devices via a browser or application installed on a desktop or laptop computer.

In one embodiment, control signals transmitted from the app or application on the user device 1210 are passed to the IoT cloud service 1220 over the Internet 1222, then forwarded from the IoT cloud service 1220 to the IoT hub 1205 and from the IoT hub 1205 to one or more of the IoT devices 1201-1204. Of course, the underlying principles of the invention are not limited to any particular manner in which the user accesses/controls the various IoT devices 1201-1204. For example, the user may transmit a control signal to turn on/off watering system IoT devices 1204.

Embodiments of the invention may include various steps, which have been described above. The steps may be embodied in machine-executable instructions which may be used to cause a general-purpose or special-purpose processor to perform the steps. Alternatively, these steps may be performed by specific hardware components that contain hard-wired logic for performing the steps, or by any combination of programmed computer components and custom hardware components.

As described herein, instructions may refer to specific configurations of hardware such as application specific integrated circuits (ASICs) configured to perform certain operations or having a predetermined functionality or software instructions stored in memory embodied in a non-transitory computer readable medium. Thus, the techniques shown in the figures can be implemented using code and data stored and executed on one or more electronic devices (e.g., an end station, a network element, etc.). Such electronic devices store and communicate (internally and/or with other electronic devices over a network) code and data using computer machine-readable media, such as non-transitory computer machine-readable storage media (e.g., magnetic disks; optical disks; random access memory; read only memory; flash memory devices; phase-change memory) and transitory computer machine-readable communication media (e.g., electrical, optical, acoustical or other form of propagated signals—such as carrier waves, infrared signals, digital signals, etc.). In addition, such electronic devices typically include a set of one or more processors coupled to one or more other components, such as one or more storage devices (non-transitory machine-readable storage media), user input/output devices (e.g., a keyboard, a touchscreen, and/or a display), and network connections. The coupling of the set of processors and other components is typically through one or more busses and bridges (also termed as bus controllers). The storage device and signals carrying the network traffic respectively represent one or more machine-readable storage media and machine-readable communication media. Thus, the storage device of a given electronic device typically stores code and/or data for execution on the set of one or more processors of that electronic device. Of course, one or more parts of an embodiment of the invention may be implemented using different combinations of software, firmware, and/or hardware.

Throughout this detailed description, for the purposes of explanation, numerous specific details were set forth in order to provide a thorough understanding of the present invention. It will be apparent, however, to one skilled in the art that the invention may be practiced without some of these specific details. In certain instances, well known structures and functions were not described in elaborate detail in order to avoid obscuring the subject matter of the present invention. Accordingly, the scope and spirit of the invention should be judged in terms of the claims which follow.

What is claimed is:

1. An Internet of Things (IoT) device comprising:
a moisture sensor to detect a moisture level;
an IoT communication interface and/or radio to wirelessly connect the IoT device to a network;
a set of pins, pads, and/or probes to electrically couple the moisture sensor to conductive elements of one or more moisture sensor attachments; and
an enclosure surrounding the moisture sensor and IoT communication interface and/or radio, the enclosure having one or more connection elements formed thereon to fixedly couple one or more moisture sensor attachments to the enclosure, thereby electrically coupling the set of pins, pads, and/or probes of the moisture sensor to the conductive elements of the moisture sensor attachments;
the conductive elements of at least one moisture sensor attachment comprising a pair of conductors to electrically engage with the set of pins, pads, and/or probes when connected to the IoT device, absorptive material between the parallel conductors to form an electrical connection between the pair of conductors when a sufficient amount of water has been absorbed;
a power source to provide power to the moisture sensor and/or the IoT communication interface and/or radio;
the IoT communication interface and/or radio to implement a low power wireless protocol to communicate with at least one IoT hub device, the IoT communication interface and/or radio to communicate a current moisture level reading to the at least one IoT hub device, and the IoT hub device to forward the current moisture level reading to an IoT service.

2. The IoT device as in claim 1 wherein the power source comprises:
a battery to provide power to the moisture sensor and/or the IoT communication interface and/or radio.

3. The IoT device as in claim 1 wherein the low power wireless protocol comprises a Bluetooth Low Energy (BTLE) protocol.

4. The IoT device as in claim 1 further comprising:
control logic to trigger one or more watering functions responsive to the current moisture level dropping to a specified low threshold and/or rising above a specified high threshold.

5. The IoT device as in claim 4 wherein the watering functions comprise turning on or off a sprinkler or other watering apparatus supplying water to an area in a vicinity of the IoT device responsive to the current moisture level dropping to the specified low threshold and/or rising to the specified high threshold.

6. The IoT device as in claim 1 further comprising:
a spike attachment adapted for insertion into soil or other material, the spike attachment comprising a pair of conductors to electrically engage with the set of pins, pads, and/or probes when connected to the IoT device; and
absorptive material to form an electrical connection between the pair of conductors when a sufficient amount of water has been absorbed.

7. The IoT device as in claim 1 wherein the enclosure comprises a circular disk.

8. The IoT device as in claim 7 wherein the circular disk is between approximately 2 to 4 centimeters in diameter and between approximately 1 to 2 centimeters thick.

9. The IoT device as in claim 8 further comprising:
a rubberized material formed around a periphery of the circular disk to form a water tight seal when the IoT device is connected to a sensor attachment.

10. The IoT device as in claim 5 wherein the control logic is configured within the IoT service, the control logic further configured to generate one or more commands to turn on or off the sprinkler or other watering apparatus, the commands being wirelessly transmitted to the IoT device from the IoT hub.

11. A system comprising:
an Internet of Things (IoT) device comprising:
a moisture sensor to detect a moisture level;
an IoT communication interface and/or radio to wirelessly connect the IoT device to a network;
a set of pins, pads, and/or probes to electrically couple the moisture sensor to conductive elements of one or more moisture sensor attachments; and
an enclosure surrounding the moisture sensor and IoT communication interface and/or radio, the enclosure having one or more connection elements formed thereon to fixedly couple one or more moisture sensor attachments to the enclosure, thereby electrically coupling the set of pins, pads, and/or probes of the moisture sensor to the conductive elements of the moisture sensor attachments
the conductive elements of at least one moisture sensor attachment comprising a pair of conductors to electrically engage with the set of pins, pads, and/or probes when connected to the IoT device, absorptive material between the parallel conductors to form an electrical connection between the pair of conductors when a sufficient amount of water has been absorbed;
a power source to provide power to the moisture sensor and/or the IoT communication interface and/or radio;
the IoT communication interface and/or radio to implement a low power wireless communication protocol to communicate with at least one IoT hub device, the IoT communication interface and/or radio to communicate a current moisture level reading to the at least one IoT hub device, and the IoT hub device to forward the current moisture level reading to an IoT service;
at least one IoT hub device comprising a wireless interface to establish a wireless communication channel with the IoT communication interface and/or radio of the IoT device using the low power wireless communication protocol, the IoT hub to further establish a communication channel over the Internet to at least one IoT service and/or user device.

12. The system as in claim 11 wherein the low power wireless communication protocol comprises a Bluetooth Low Energy (BTLE) protocol.

13. The system as in claim 11 further comprising:
control logic to trigger one or more watering functions responsive to the current moisture level dropping to a specified low threshold and/or rising above a specified high threshold.

14. The system as in claim 13 wherein the watering functions comprise turning on or off a sprinkler or other watering apparatus supplying water to an area in a vicinity of the IoT device responsive to the current moisture level dropping to the specified low threshold and/or rising to the specified high threshold.

15. The system as in claim 11 further comprising:
a spike attachment adapted for insertion into soil or other material, the spike attachment comprising a pair of conductors to electrically engage with the set of pins, pads, and/or probes when connected to the IoT device; and
absorptive material to form an electrical connection between the pair of conductors when a sufficient amount of water has been absorbed.

16. The system as in claim 11 wherein the enclosure comprises a circular disk.

17. The system as in claim 16 wherein the circular disk is between approximately 2 to 4 centimeters in diameter and between approximately 1 to 2 centimeters thick.

18. The system as in claim 17 further comprising:
a rubberized material formed around a periphery of the circular disk to form a water-tight seal when the IoT device is connected to a sensor attachment.

19. The system as in claim 14 wherein the control logic is configured within the IoT service, the control logic further configured to generate one or more commands to turn on or off the sprinkler or other watering apparatus, the commands being wirelessly transmitted to the IoT device from the IoT hub.

* * * * *